(12) United States Patent
Wernze et al.

(10) Patent No.: US 11,003,676 B2
(45) Date of Patent: May 11, 2021

(54) SOFTWARE INTEGRATION OBJECT LINKING DATA STRUCTURES

(71) Applicant: SAP SE, Walldorf (DE)

(72) Inventors: Frank Wernze, Staad (CH); Gerhard Schick, St. Ingbert (DE)

(73) Assignee: SAP SE, Walldorf (DE)

(*) Notice: Subject to any disclaimer, the term of this patent is extended or adjusted under 35 U.S.C. 154(b) by 498 days.

(21) Appl. No.: 15/906,258

(22) Filed: Feb. 27, 2018

(65) Prior Publication Data

US 2019/0266275 A1 Aug. 29, 2019

(51) Int. Cl.
| | | |
|---|---|---|
| *G06F 7/00* | (2006.01) | |
| *G06F 17/00* | (2019.01) | |
| *G06F 16/2458* | (2019.01) | |
| *G06F 16/28* | (2019.01) | |
| *G06F 16/22* | (2019.01) | |
| *G06F 16/23* | (2019.01) | |
| *G06F 16/2453* | (2019.01) | |

(52) U.S. Cl.
CPC ...... *G06F 16/2474* (2019.01); *G06F 16/2228* (2019.01); *G06F 16/2379* (2019.01); *G06F 16/24539* (2019.01); *G06F 16/288* (2019.01); *G06F 16/289* (2019.01)

(58) Field of Classification Search
CPC ............... G06F 16/2474; G06F 16/289; G06F 16/2379; G06F 16/2228; G06F 16/288
USPC ........................................................ 707/715
See application file for complete search history.

(56) References Cited

U.S. PATENT DOCUMENTS

| | | | | |
|---|---|---|---|---|
| 5,542,078 | A  * | 7/1996 | Martel | G06F 16/289 |
| 7,725,371 | B2 | 5/2010 | Wernze et al. | |
| 8,527,411 | B2 | 9/2013 | Wernze et al. | |
| 9,665,270 | B2 * | 5/2017 | Deb | G06F 3/04855 |
| 10,437,840 | B1 * | 10/2019 | Poh | G06F 16/24578 |
| 2002/0165724 | A1 * | 11/2002 | Blankesteijn | G06F 16/2308 705/1.1 |
| 2005/0086360 | A1 * | 4/2005 | Mamou | G06F 16/254 709/232 |
| 2007/0192348 | A1 * | 8/2007 | Brodersen | G06F 16/284 |
| 2007/0226730 | A1 * | 9/2007 | Coyle | G06F 16/289 717/170 |
| 2008/0133406 | A1 | 6/2008 | Wernze et al. | |
| 2008/0243654 | A1 | 10/2008 | Wernze et al. | |
| 2013/0060371 | A1 * | 3/2013 | Kienzle | G06Q 10/06316 700/100 |

(Continued)

*Primary Examiner* — Binh V Ho

(74) *Attorney, Agent, or Firm* — Klarquist Sparkman, LLP

(57) ABSTRACT

Techniques and solutions are described for providing integration objects that can be used to enhance data retrieval, and can be used to provide shared data access for multiple applications, and to allow access to application functionality through an interface. The integration object includes a plurality of integration data objects, at least a portion of which are mapped to data objects stored in one or more data sources. The integration data objects can hold values stored in correspondingly mapped locations of the data objects, such as in a value field. A reference field of the integration data objects can hold reference information regarding a location of a value in a respectively mapped data source. At least a portion of the integration data objects can include a defined sequencing with one or more other integration data objects.

20 Claims, 16 Drawing Sheets

(56) References Cited

U.S. PATENT DOCUMENTS

| | | | |
|---|---|---|---|
| 2013/0325790 A1* | 12/2013 | Srinivasan | G06F 16/252 |
| | | | 707/602 |
| 2014/0233917 A1* | 8/2014 | Xiang | H04S 7/30 |
| | | | 386/285 |
| 2016/0092499 A1* | 3/2016 | Leigh | G06F 8/34 |
| | | | 707/740 |
| 2016/0314155 A1* | 10/2016 | Wilson | G06F 16/254 |
| 2017/0132302 A1* | 5/2017 | Johny | G06F 16/27 |
| 2017/0344592 A1* | 11/2017 | Sundaram | G06F 16/256 |
| 2019/0347614 A1* | 11/2019 | Khasis | G01C 21/3415 |

* cited by examiner

620

INTEGRATION OBJECT MAINTENANCE LOG — 621

| Integration Object Name | | Service Status Profile | | Integration Object Action | |
|---|---|---|---|---|---|
| Reference Business Object | | Stage Freight Order | | Integration Object Validation | |
| Reference Business Object Type | /SCMTMS/TOR | | | Integration Object Determination | |

622

| Pos. | Int. Obj. Name | Reference BO | Int. Obj. Action | Int. Obj. Determination | Int. Obj. Validation |
|---|---|---|---|---|---|
| ◄ | ◄ | ◄ | ◄ | ◄ | ◄ |
| ◄ | ◄ | ◄ | ◄ | ◄ | ◄ |

[ Refresh ] [ Save ] [ Save & Exit ] [ Add Action/Determination and Validation ] [ Cancel ]

Integration Object Header Definition — 623

| Integration Object Header ID | | Free Customer Field 1 | |
|---|---|---|---|
| Integration Object Type | | Free Customer Field 2 | |
| Integration Object Status | | Integration Object Valid From | |
| Integration Object Version | | Integration Object Valid To | |

Integration Object Item Definition

624

| Pos. | Int. Obj. Item ID | Int. Obj. Sub. Item ID | Int. Obj. ID | Int. Obj. Type | Int. Obj. Status | Int. Obj. Valid To | Cust. Field 1 |
|---|---|---|---|---|---|---|---|
| ◄ | ◄ | ◄ | ◄ | ◄ | ◄ | ◄ | ◄ |
| ◄ | ◄ | ◄ | ◄ | ◄ | ◄ | ◄ | ◄ |
| ◄ | ◄ | ◄ | ◄ | ◄ | ◄ | ◄ | ◄ |
| ◄ | ◄ | ◄ | ◄ | ◄ | ◄ | ◄ | ◄ |

[ Add Int. Obj. Item ] [ Add Int. Obj. Sub. Item ]

625

| Integration Object Item ID | | Free Customer Field 1 | |
|---|---|---|---|
| Integration Object Sub. Item ID | | Free Customer Field 2 | |
| Integration Object ID | | Integration Object Valid To | |
| Integration Object Type | | Integration Object Valid From | |
| Integration Object Status | | | |

Fig. 6B

SOFTWARE INTEGRATION OBJECT LINKING DATA STRUCTURES

FIELD

The present disclosure generally relates to data warehouses, databases, and data access. Particular implementations relate to integration objects for directly accessing complex data structures and reducing hardware system utilization or load, and integration objects acting as integration reference layers for staging data access and software application or process communication or interaction.

BACKGROUND

Massive data warehouses storing vast amounts of data are increasingly common. Accessing such data can be difficult or resource-intensive, especially when large amounts of distinct sets of data must be accessed near-simultaneously. This may lead to massive CPU load or low system performance, even with hardware and software optimizations. Further, such data warehousing systems may be well designed for long-term data storage, but not for specific uses of the stored data. Thus, there is room for improvement.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Techniques and solutions are described for providing integration objects that can be used to enhance data retrieval, and can be used to provide shared data access for multiple applications, and to allow access to application functionality through an interface. The integration object includes a plurality of integration data objects, at least a portion of which are mapped to data objects stored in one or more data sources. The integration data objects can hold values stored in correspondingly mapped locations of the data objects, such as in a value field. A reference field of the integration data objects can hold reference information regarding a location of a value in a respectively mapped data source. At least a portion of the integration data objects can include a defined sequencing with one or more other integration data objects.

According to one aspect, a method is provided for processing data requests using an integration object. The method can be in conjunction with, or by, an application having first access pathways to values associated with one or more data sources. The data sources can represent analog world objects, and actions or processes involving analog world objects.

The first access pathways can represent a direct or default access pathway to the data object, which can be through a first interface of the one or more data sources, which does not involve accessing the integration object. The first access pathway and interface can be, for example, issuing a query to a database system through an interface to the database system (e.g., an application that generates or issues queries to the database system). The application can have second access pathways to the values of the data sources through the integration object.

A plurality of data objects are identified. At least a portion of the plurality of data objects are stored in the one or more data sources. The plurality of data objects comprise one or more values. The integration object is identified. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At least a portion of the data values are retrieved from the plurality of data objects. The at least a portion of the data values are stored into correspondingly mapped fields of the integration object. An update is received to the sequencing relationship of two or more integration data objects of the at least a portion of the integration data objects. The sequencing relationship between the two or more integration data objects of the plurality of integration data objects is updated. A request is received to process values of a plurality of integration data objects to provide a result. The values are processed to generate the result. The result is returned. Applying the updated sequencing relationship of the two or more integration data objects provides enhanced data retrieval performance (e.g., reduced execution time, memory use, CPU use, network use, or a combination thereof).

According to another aspect, a method is provided for providing shared access to data in an integration object. The data sources can represent analog world objects, and actions or processes involving analog world objects. A plurality of data objects are identified. At least a portion of the plurality of data objects are stored in the one or more data sources. The plurality of data objects comprise one or more values. The integration object is identified. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At least a portion of the data values are retrieved from the plurality of data objects. The at least a portion of the data values are stored into correspondingly mapped fields of the integration object. An update is received to the sequencing relationship of two or more integration data objects of the at least a portion of the integration data objects. The sequencing relationship between the two or more integration data objects of the plurality of integration data objects is updated. A request is received from a first application to process values of a plurality of integration data objects to provide a result. The values are processed to provide the result. The result is returned. Applying the updated sequencing relationship of the two or more integration data objects provides enhanced retrieval performance compared with accessing the data sources. The result is processed to provide a result value. The result value is stored in a field of an integration data object of the integration object. A request is received from a second application for the stored result value. The stored result value is retrieved from the integration data object. The stored result value is returned to the second application.

In a further aspect, a method is provided for implementing an interface layer. The data sources can represent analog world objects, and actions or processes involving analog world objects. A plurality of data objects are identified. At least a portion of the plurality of data objects are stored in the one or more data sources. The plurality of data objects comprise one or more values. The integration object is identified. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At least a portion of the data values are retrieved from the plurality of data objects. The at least a portion of the data values are stored into correspondingly mapped fields of the integration object. An update is received to the sequencing relationship of two or more integration data objects of the at least a portion of the integration data objects. The sequencing relationship between the two or more integration data objects of the plurality of integration data objects is updated. A first request is received from a first application to process values of a plurality of integration data objects to provide a first result. Functionality of at least a second application is called and performs the requested processing to generate the first result. The first result is returned in response to the first request. Applying the updated sequencing relationship of the two or more integration data objects provides enhanced data retrieval performance compared with accessing the data sources and the interface layer makes functionality of the second application available to the first application. The first result is processed. Based at least in part on the processing, a first updated value is generated to be stored in a data source of the one or more data sources or in the integration object.

The present disclosure also includes computing systems and tangible, non-transitory computer readable storage media configured to carry out, or including instructions for carrying out, an above-described method. As described herein, a variety of other features and advantages can be incorporated into the technologies as desired.

The foregoing and other objects, features, and advantages of the invention will become more apparent from the following detailed description, which proceeds with reference to the accompanying figures.

BRIEF DESCRIPTION OF THE DRAWINGS

FIG. 6B depicts an example user interface screen for creating, defining, maintaining or viewing an integration object.

DETAILED DESCRIPTION

Figure 1:
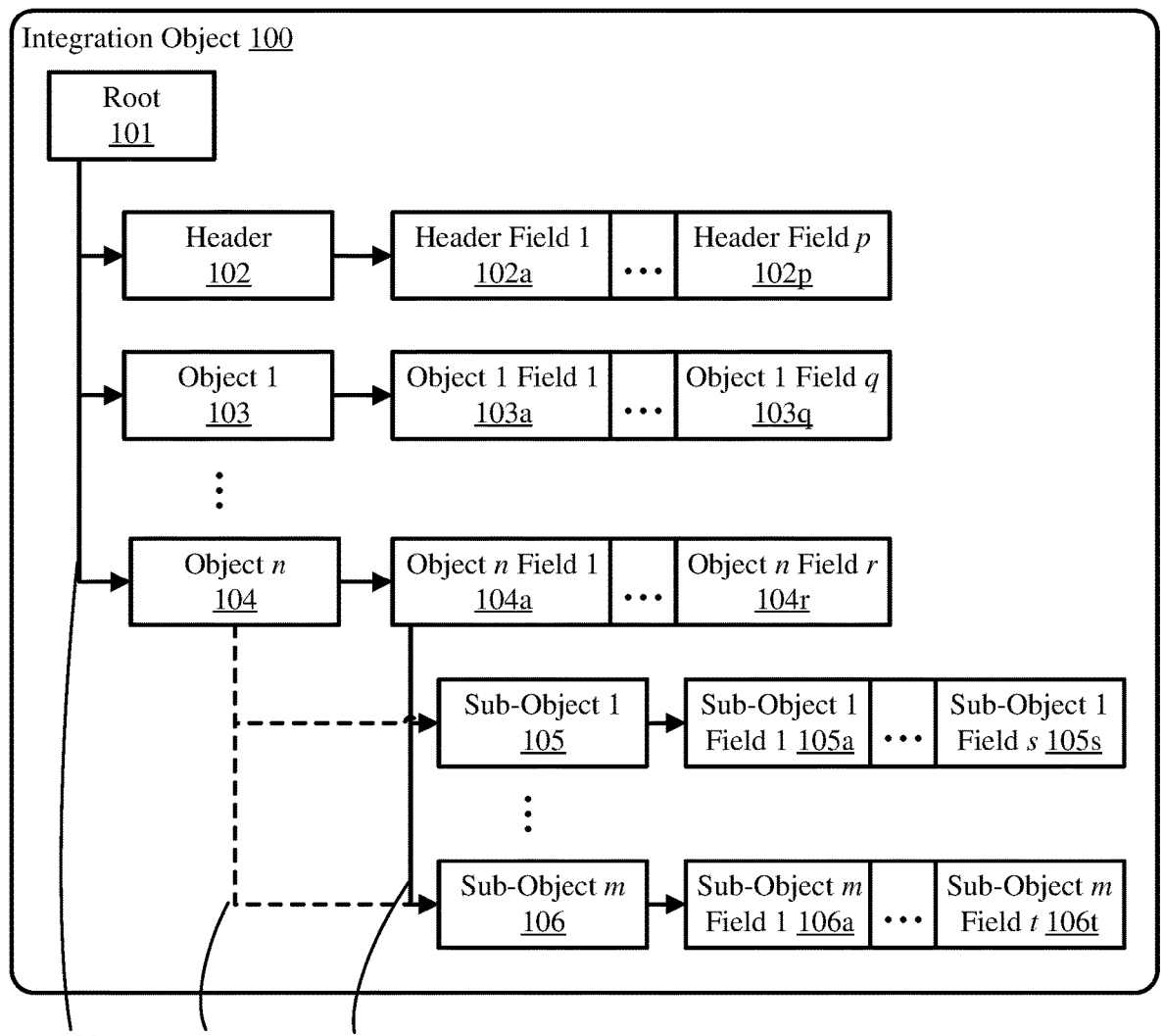
FIG. 1 is a schematic diagram depicting an integration object.

A variety of examples are provided herein to illustrate the disclosed technologies. The technologies from any example can be combined with the technologies described in any one or more of the other examples to achieve the scope and spirit of the disclosed technologies as embodied in the claims, beyond the explicit descriptions provided herein. Further, the components described within the examples herein may be combined or recombined as well, as understood by one skilled in the art, to achieve the scope and spirit of the claims.

Example 1—Integration Object Overview

An integration object may be provided for improving performance of software application processes handling massive amounts of data and providing fast data access, up-to-date data, or real-time information associated with the data. One or more applications may use an integration object to access data (which data can be, in some cases, all or a portion of an instance of a complex or abstract data type), data files, data structures or complex data structures, or data sources. In a particular example, the integration object can be used to access data in a logical data object, such as a logical data object as described in Example 16. In addition to data, the integration object can be used to access operations associated with a logical data object or other type of data object.

Further, the integration object may be used as an intermediate layer when accessing complex data structures, and may store data from an application, from one or more data structures, or data from a data structure updated by an application, thus providing access to data without requiring the process actually access the data structure. Further, the integration object may be used as a reference layer between applications, both of which may access the integration object in place of the data structures. In this way, an integration object may function in place of complex data sources or data structures, and may allow for faster data access between an application and a data structure, or between two applications.

Further, the integration object may later update the data structures with any updated or new data it has received from one or more applications. Thus, the use of the integration object may provide flexible data updates to a data source, such as performing updates during low system usage and thereby avoiding overloading system resources, such as excess CPU utilization or bandwidth usage, and performing more efficient updates.

A few example implementations are as follows. In one embodiment, an integration object may be implemented as an object class, having data fields or attributes and actions (methods or functions). Such an object class may be instantiated to hold specific data or data objects as described herein. In another embodiment, an integration object may be implemented as a data structure such as a collection of arrays or linked lists, which may have associated actions in some scenarios. In further aspects, an integration object can be a data structure (e.g. array, tree, queue, linked list, heap, graph, etc.) of integration data objects, where an integration data object can be an instance of an abstract data type (e.g., having particular data members, or fields, and optionally one or more methods). In other embodiments, the integration object may be implemented in XML, or other tree data file.

An integration object, or use of multiple instances of varying integration objects, may provide a mirrored reality with constant access to the actual reality in terms of content or data stored in complex data structures. Such a mirrored reality can enable creation of additional applications (e.g. strategic planning, infrastructure optimization) or additional functionality (e.g. simulation, version management), which may have additional or new complex data structures, in addition to existing data structures, being mirrored by the integration objects as well as traditional or pre-existing programs or functionality.

Using integration objects to create such a mirrored reality can have the further advantage, in addition to performance increases, to enhance existing applications with independent applications that may provide real-time planning or optimization functionality. This is possible due to the simplicity of the integration objects compared to the complexity of the complex data structures being mirror by the integration objects. This further allows multiple applications to work with the same data content simultaneously without performance or read/write limitations that may be incurred by actually using the underlying complex data structures simultaneously. Thus, in place of updating or changing an existing application or functionality, instead one or more integration objects may be defined for new functionality based on the underlying data structures and a new integration layer providing the additional functionality may be added without affecting existing functionality. Such an approach can both enhance application functionality, while maintaining the current available functionality, and effectively manage application architecture scope through effective modularization of functionality and data availability. It can further allow for legacy software to be used in conjunction with new versions to simplify transition between versions.

Example 2—Integration Object

FIG. 1 depicts an integration object 100. The integration object may have a root 101. From the root 101, the integration object 100 may have a header object 102. The header object 102 may define, at least in part, the integration object 100. The root 101 may be integrated, in full or in part, with the header object 102. The header object 102 may have one or more header fields, such as header field 1 102a through header field p 102p. The header fields 102a-p may be data fields and may contain data defining the integration object 100. Data that defines the integration object may include an identifier for the integration object, a type, a category, a location for the integration object to be stored, a version, or any other data that designates characteristics about the integration object.

From the root 101, the integration object 100 may have one or more data or pointer objects, such as object 1 103 through object n 104. Each object 103-104 may have one or more fields. For example, object 1 103 may have one or more fields, object 1 field 1 103a through object 1 field q 103q, and object n 104 may separately have one or more fields, object n field 1 104a through object n field r 104r. The object fields, 103a-q and 104a-r, may contain data (such as a variable, a value of a variable, or a constant), pointer data (such as a pointer variable or a memory address for data), references (such as an address for a data source, a document, an interface location, or a link), or combinations thereof, or portions thereof (for example, reference such as a URI may be split into two fields, one holding a root address and the other holding an extension to the root address). Generally, the object fields relate to or define their object, or point to or reference additional data that relates to or defines their object. In some scenarios, several fields in aggregate will point to or reference additional data.

In some cases, the integration object 100, such as via fields of the integration data objects 103-104 can be used to directly read a value of data object of a data source, such as a logical data object stored in the data sources. For example, the field can include reference or mapping information which can be used to directly access a memory or storage (e.g., disk) location having a value. Or, the field or mapping information can be used to call methods associated with a data object, such as a logical data object. In some cases, the value can be ready directly from the referenced or mapped location when the integration object 100 is accessed. In other cases, the value can be stored in the integration data object. The mapping or reference information can identify the data source, but may or may not be useable to access the value. In cases where the value can be accessed by the reference or mapping information, and the value is also stored in the integration object, the value can be periodically reread from the data source and the stored value updated, which update can occur via a process of the integration data object or by an external process.

In cases where the objects 104 include reference or mapping information that can directly access a value of a data object, such as a logical data object, data processing performance can be improved. For example, a logical data object may contain more fields or actions than are needed for the integration object 100, and using the logical data object directly may involve updating more records or performing more processes than necessary by directly accessing the mapped or referenced locations of the integration data object (e.g., by dereferencing logical pointers stored in fields of the objects 103-104). As an example, updating the logical data object may involve complex joins from multiple database tables. Even if the database tables are in memory, performance can be reduced when a large number of logical data objects are to be processed.

In some cases, reference or mapping information can provide read access to data from a data object, such as a logical data object. That is, while the logical (or physical) pointer can be references to access a current value, updating the value in the integration object does not replace or modify the value in the mapped/referenced location. In other cases, the mapping or reference information can be used to provide read/write access, where updates to the information in the referenced/mapped value can be automatically updated, or can be updated upon receiving a command (e.g., a "commit" request) to push an updated value to the mapped or reference data object. Some embodiments may not include writing to a data source, which may increase the performance benefit from using objects in an integration object in place of the data source; other embodiments may include limited or controlled writes to a data source, such as scheduling writes during low-use times or writing only certain values or fields back to a data source.

As will be further described, in at least some cases, an integration data object, or field thereof, is not mapped to a data object. Or, a field can be selectively mapped, such as pushing data to the data source upon request. Fields that are not mapped to the data source, or not automatically pushed, can be useful to provide independent functionality using the integration data objects (e.g., changes can be made, or simulations performed without modifying underlying data).

An object in the integration object 100, such as object n 104, may have one or more sub-objects, such as sub-object 1 105 through sub-object m 106. The sub-objects 105-106 are generally similar to objects 103-104, but are related 110a to a specific object in the integration object 100, rather than related to the integration object at the root 101 level. A sub-object 105-106 may be related 110a to its parent object 104 through an object field of the parent object, such as object n field 1 104a. Alternatively, sub-objects may be related 110b to the parent object directly, rather than through a field of the parent object. In other scenarios, sub-objects may be related to the parent object through different fields of the parent object.

Sub-objects may have one or more fields. For example, sub-object 1 105 may have one or more fields, such as sub-object 1 field 1 105a through sub-object 1 field s 105s, and sub-object m 106 may separately have one or more fields, such as sub-object m field 1 106a through sub-object m field t 106t. The sub-object fields, 105a-s and 106a-t, may contain data (such as a variable, a value of a variable, or a constant), pointer data (such as a pointer variable or a memory address for data), references (such as an address for a data source, a document, an interface location, or a link), or combinations thereof, or portions thereof (for example, reference such as a URI may be split into two fields, one holding a root address and the other holding an extension to the root address). Generally, the sub-object fields relate to or define their sub-object, or point to or reference additional data that relates to or defines their sub-object. Sub-objects may further have their own sub-objects, similar to objects, with their own respective sub-sub-object fields, and so on.

In some scenarios, several fields in aggregate will point to or reference additional data. For example, a data source or data structure may be accessible using reference pathways, such as a URI or URL. One field may provide an address path to a node with multiple data fields, and a second field may specify which data field to access. In another example, the address path may be divided into two fields, such as a field with a root address and a second field with an extension for the root address. In another example, a field may contain the name of a system to call (containing the data source or data structure) or a function to use to call a system, a second field may contain a username for accessing the system, and a third field may contain a password for accessing the system.

An integration object 100 may put arbitrary items, represented by objects or sub-objects, into relationships. An integration object 100 may contain references 108, 110a-b between objects or sub-objects, which may represent relationships between the objects or sub-objects. In some embodiments, the order (or sequence) of objects or sub-objects, as represented by the references 108, 110a-b, may be relevant. For example, the order may represent a hierarchy, preference, or an order in which to process the objects or sub-objects. In some embodiments, an object or sub-object may have more than one reference or relationship. For example, sub-object 1 105 may have a relationship 110a-b with object n 104, but may also have a relationship with object 1 103, such as by reference through one of its fields. In some embodiments, manipulating or changing the integration object 100 may only include adding or removing objects or sub-objects and changing the relationships between the objects and sub-objects within it, without changing the objects themselves (e.g. such as changing the data in the objects' fields).

In some cases, a sequencing can represent an order in which integration data objects should be processed, which can represent a series of sequential steps in an analog word process (e.g., a series of handling steps or steps in an itinerary or route). In other cases, a sequencing can represent an ordering, such as a physical order, of objects, such as analog world objects (e.g., an order in which rail cars or containers are stored in a linked or other ordered arrangement).

In some cases, in addition to having relationships between integration data objects, an integration object, or an integration data object thereof, can reference another integration object. For example, each integration object can have a unique identifier (and, optionally, a physical or logical pointer than can be used to access the integration object).

In at least certain aspects, disclosed technologies can facilitate the update of a relationship, such as a hierarchical or sequencing relationship between integration data object. Updating the integration data objects, and optionally the underlying data objects, in this manner can provide performance improvement compared with working directly with the underlying data objects (e.g., logical data objects). For instance, when a relationship between two integration data objects changes which corresponds to a change in relationship between two different logical data objects, updating the logical data objects can require updating the entire logical data object, such as reading multiple underlying database tables for each logical data object, processing the information, updating the information, and storing the information back in the tables. Using the integration object, the needed data can be read directly from the integration object (e.g., via reading a stored value or dereferencing a physical or logical pointer in real-time). In some cases, updated data can be stored back to the logical data object (or other data object), including to a particular database table, including selectively upon receiving a command to update the data object (e.g., a commit, write, or push request). In some cases, pushing updates to the data sources can provide enhanced data performance compared with reading/updating data via an application that directly manipulates the data objects referenced by an integration data object. Using the integration data object can also decouple the data of the data objects from a software application which natively uses the data objects (e.g., which typically creates or manipulates the data objects).

In a particular aspect, a sequencing step (which can be represented by an integration data object or a relationship between integration data objects to be processed in the sequencing step) can be applied concurrently to a plurality of other integration data objects. That is, an integration data object representing a sequence step or process step can include processed integration data objects as children (e.g. sub-integration data objects) or via another relationship. In some cases, different processing steps can be performed by different applications, which different applications can both access, including in some cases, concurrently accessing, the integration object and particular integration data objects thereof. In more particular aspects, the completion of a first sequence step by a first software application can trigger a second software sequence step performed by a second application. In some cases, the first, second, or both applications can also directly access data objects associated with the integration data object (e.g., via a mapping), a portion of such data objects. In other cases, the first, second, or both applications only access data from the data objects, or a portion thereof, via the integration data object.

An integration object 100 may be implemented as a programming data object that may be stored in memory and available to one or more processes or software applications. An integration object 100 may be a data file (e.g. schema file), a data document (e.g. XML document), a lightweight data object, linked data objects, or any other suitable software implementations. Further, each object or sub-object in an integration object may also have its own database assigned, with multiple database tables, or other data source.

In some embodiments, the object and sub-objects may be representations of larger objects in data sources. The integration object 100 may allow for manipulation of these objects without accessing the objects in the data sources (other than, for example, access to initially populate values in the integration object). This may improve the speed of manipulation of these objects and reducing resource utilization by reducing calls to the data sources to manipulate the objects.

In some embodiments, the fields of each object may be limited to identifying information for the object. For example, an object such as object 1 103 may only have fields that store identifying information for the larger object stored in the data source. In some cases, this may be a single identifier field storing a unique ID for the object, or it may be a set of fields, such as an identifier field, a type field, and a category field, which, when put together, uniquely identify the object in the data source. Such a field or set of fields may be the primary key for the object in its data source. Storing only the primary key fields for an object in the integration object 100 may improve performance by reducing the size of the integration object. Having the primary key available in the integration object 100 may also improve performance when accessing the data source using the primary key from the integration object by allowing direct access to the object in the data source with reduced, minimal, or no searching.

In some embodiments, the order of objects 103-104 within the integration object 100, or sub-objects 105-106 under an object, may not be important. In such cases, the objects may be sorted by an application when it uses the integration object 100; such sorting may be based on one or more fields of each object in the integration object. Such sorting may also be done separately or iteratively for sub-objects for an object, and so on; for example, an application may sort all the objects in an integration object and then sort all the sub-objects under a single object or sort all the sub-objects under each respective object, or only the sub-objects under a given object, or some combination thereof. Generally, the sorting will not affect or change the relationships 108, 110*a-b* between the objects 103-104 in the integration object 100, and may be based, at least in part, on the relationships of the objects and sub-objects. This also allows for sorting flexibility, based on different sorting needs of an application at different times or for different functionality.

In some embodiments, functionality may be available in an application using a program to put objects or sub-objects into relationships. For example, an application may manipulate an integration object 100 to place object 1 103 into a relationship with object n 104 by making object 1 103 a sub-object of object n 104. In another example, object 1 103 may be made a sub-object of sub-object 1 105, thus placing the two objects in a relationship.

Further, such sorting and relationship functionality means that when a new object is added to an integration object, it does not need to be added in a particular order or in a particular relationship to other objects. Order may be determined later based on sorting, and relationships may be determined and set later based on application need, including by comparing integration objects having different structures (e.g., by comparing an integration object for a train, with integration objects for railcars of the train, with integration objects for a train itinerary or stations along an itinerary).

In some embodiments, an application may group various objects or sub-objects together in an integration object. Such grouping may not be represented in the integration object, but may involve a mix of the relationships between objects and sub-objects and sorting done on the objects in the integration object.

Example 3—Integration Object with External Mapping

Figure 2A:
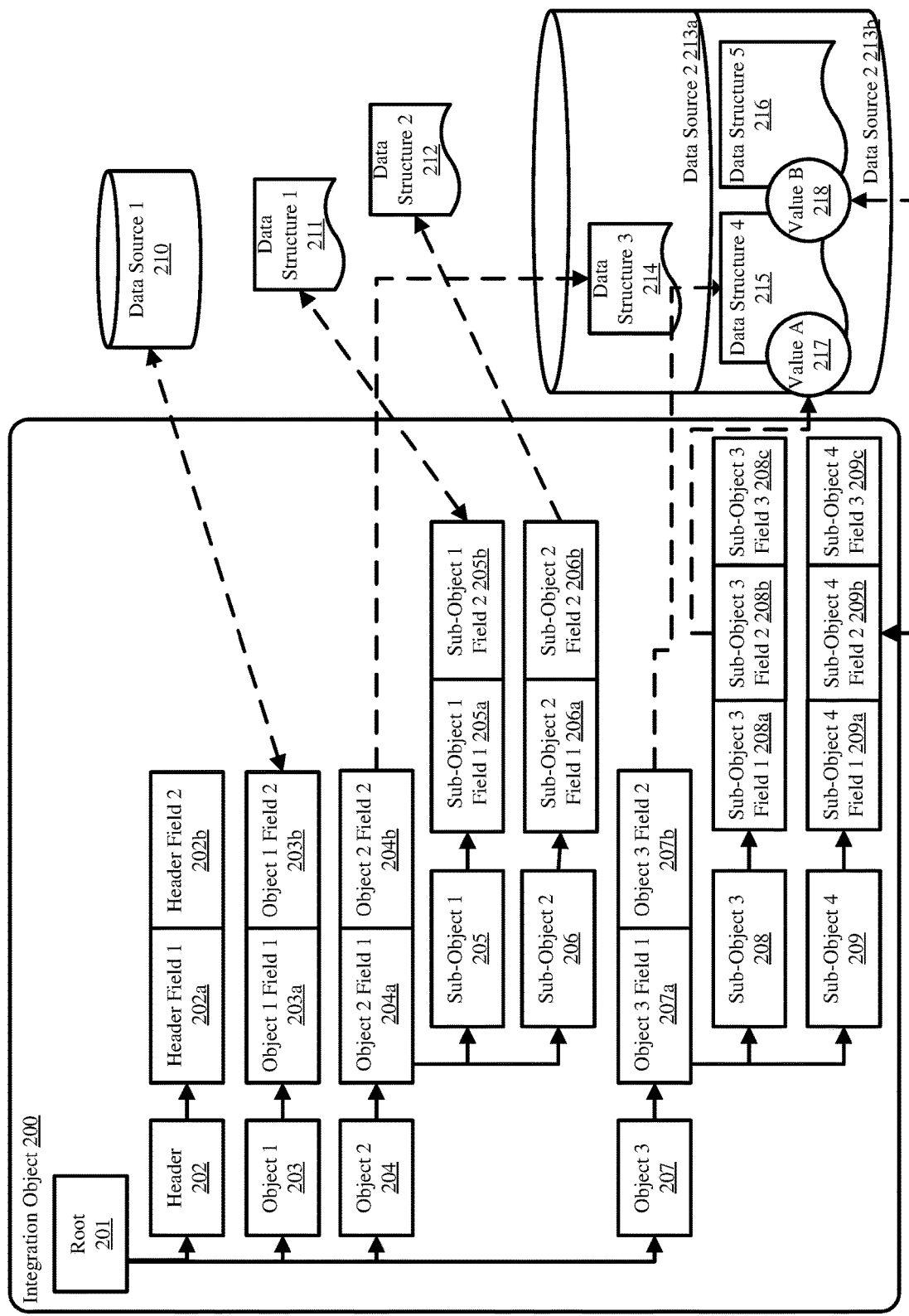
FIG. 2A is a schematic diagram depicting an integration object with external mappings.

FIG. 2A illustrates an integration object 200 with pointer objects mapped to outside data sources. The integration object 200 may be the integration object 100 of FIG. 1. The integration object 200 may have a root 201, a header 202 with header field 1 202*a* and header field 2 202*b*, and objects 1-3 203, 204, 207. Object 1 203 may have two fields, object 1 field 1 203*a* and object 1 field 2 203*b*. Object 1 field 2 203*b* may be mapped to data source 1 210. For example, object 1 field 2 203*b* may contain pointer or reference data for locating or accessing data source 1 210; such data may be a URL or URI, a memory address for data source 1, port/socket information, a network address, or other data suitable for use in accessing or communicating with data source 1. Object 1 field 1 203*a* may contain data from data source 1 210, such as a variable (which may be retrieved from data source 1 210 and stored in object 1 field 1 203*a*), or data about data source 1, such as part of the information needed to map object 1 203 to data source 1 via object 1 field 2, or data related to data source 1 but not actually from data source 1, such as data from a different source that may be placed in data source 1.

A data source may include a data warehouse, a database or a database management system, a data document (e.g. XML document), a data file (e.g. a schema file), a heap, a business object (or logical data object), or any other suitable repository for data or data source in a semantic layer. A data source may further include any specific data structure or data source within a data source, such as a data file stored within a database.

Mapping may include having or including pointer (which can be a logical pointer or a physical pointer) or reference data to the mapped item or location, or receiving or obtaining data from the mapped source, structure, or field, or otherwise linking the data objects. For example, an object mapped to a field may contain pointer or reference data for accessing the field, or may contain data from that field, put data into that field, receive data from that field, or may otherwise be linked to that field. Mapping may be unidirectional or bidirectional. Generally, unidirectional mapping will map a field from the integration object 200 to a data source, data structure, or value, as described above. Bidirectional mapping may be allowed in some cases, where a value stored in a field in the integration object may be provided to the mapped data source, data structure, or value, such as through a push or a store or update routine.

Object 2 204 may have fields object 2 field 1 204a and object 2 field 2 204, respectively similar to the fields of object 1 203. Object 2 field 2 204b may be mapped to a data structure, such as data structure 3 214. A data structure may be included within, or be a part of, or be accessible through, a data source; for example, data structure 3 214 may be included in a particular portion of data source 2 213a. Object 2 field 2 203b may contain pointer or reference data for locating or accessing data structure 3 214; such data may be a URL or URI, a memory address for data structure 3, port/socket information, a network address, a node identifier, a database table or view identifier, a database stored procedure identifier, a row or column identifier, or other data suitable for use in accessing or communicating with data structure 3.

A data structure may include any structure within a data source, such as a table, a view, or a stored procedure in a database, a tree structure or a sub-tree (e.g. node-leaf), a heap, a linked list or hierarchical list, a business object or sub-object (or logical data object), or any suitable arrangement of data in a data source or semantic layer. A data structure may include a row having one or more columns in a table in a database, or a column having one or more rows in a table in a database. A data structure may be a complex data structure, which may include multiple separate structures linked together, nested, or otherwise arranged to store related data or reference each other. A data structure may be a field, such as a leaf node in a tree structure or a cell in a table.

Object 2 204 may have sub-objects, such as sub-object 1 205 and sub-object 2 206 linked through object 2 field 1 204a. Sub-object 1 may have fields sub-object 1 field 1 205a and sub-object 1 field 2 205b, which may be similar to other object fields as described herein. Sub-object 1 field 2 205b may be mapped to data structure 1 211. Data structure 1 211 may be a data structure as described herein, and may part of a data source different from data source 1 210 or data source 2 213a, 213b, or may be a data source in itself. Similarly, sub-object 2 206 may have fields sub-object 2 field 1 206a and sub-object 2 field 2 206b, which may be similar to other object fields as described herein. Sub-object 2 field 2 206b may be mapped to a different data structure, such as data structure 2 212, which may be similar to other data structures as described herein. An object or sub-object may be mapped to a data structure or data source also mapped to by another object or sub-object. For example, sub-object 2 206 may be alternatively mapped to data structure 1 211 via sub-object 2 field 2 206b, while sub-object 1 205 is also mapped to data structure 1.

Object 3 207 may have fields object 3 field 1 207a and object 3 field 2 207b, which may be similar to fields described herein. Object 3 field 2 may be mapped to data structure 4 215 in a portion of data source 2 213b, which may be separate from the portion of data source 2 213a containing data structure 3 214.

Object 3 207 may have sub-objects sub-object 3 208 and sub-object 4 209 linked to through object 3 field 1 207a. Sub-object 3 208 may have fields sub-object 3 field 1 208a, sub-object 3 field 2 208b, and sub-object 3 field 3 208c, which may be similar to fields as described herein. Sub-object 3 field 2 208b may be mapped to value A 217. Value A 217 may be included in, or accessible through, or a part of, data structure 4 215. Alternatively, Value A 217 may be included in, or accessible through, or part of, data source 2 213b, or through some other complex data structure within data source 2 213b.

Sub-object 4 209 may have fields sub-object 4 field 1 209a, sub-object 4 field 2 209b, and sub-object 4 field 3 209c, which may be similar to fields as described herein. Sub-object 4 field 2 209b may be mapped to value B 218. Value B 217 may be included in, or accessible through, or a part of, data structure 4 215 or, similarly, data structure 5 216 (or both). Alternatively, Value B 218 may be included in, or accessible through, or part of, data source 2 213b, or through some other complex data structure within data source 2 213b.

A value may include a data value, such as a value calculated by an application or provided by a database (such as the value of a particular database field of a particular database table, a particular record e.g., row, selection of database information e.g. a table or particular columns or rows, or query results), a variable, or a pointer variable or other value that references a data source, data structure, a complex or abstract data type (which may include multiple values), or other value.

Example 4—Integration Object with Specific Data Structure

Figure 2B:
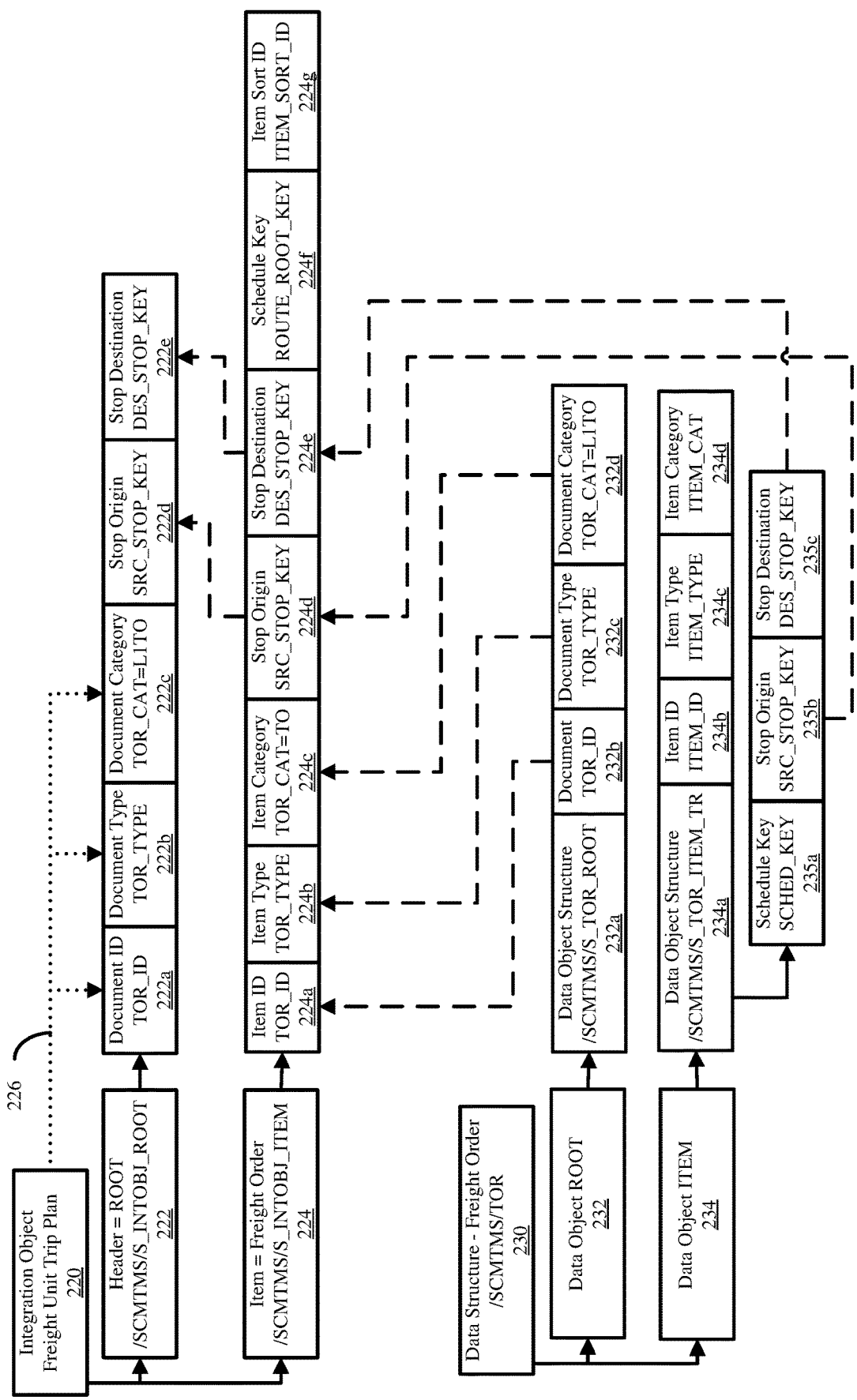
FIG. 2B illustrates a specific example of an integration object with partial mapping to a complex data structure.

FIG. 2B illustrates a specific example of an integration object 220 partially mapped to a complex data structure 230. The integration object 220 may be instantiated for a freight unit trip plan. The integration object 220 may have a header 222 that may be defined as a root and contain a URI, such as/SCMTMS/S_INTOBJ_ROOT, for identifying the location of the integration object. The header 222 may have fields Document ID 222a, Document Type 222b, Document Category 222c, Stop Origin 222D, and Stop Destination 222e. Some header fields may be set when the integration object 220 is instantiated; for example, Document ID 222a, Document Type 222b, and Document Category 222c may be populated with values 226 when the integration object 220 is created or instantiated. Some header fields, such as the initially populated fields 222a-c, may define the integration object 220, which may be a data document. The values for such header fields 222a-c may be provided 226 in response to user input, provided 226 as formal parameters when the object is created or instantiated, or may be auto-populated 226, such as based on particular rules or settings for a particular application that will use the integration object or for a particular type of integration object.

The integration object 220 may have one or more objects or items, such as the item 224 defined as a freight order with a representative URI for accessing the item directly, such as/SCMTMS/S_INTOBJ_ITEM. The freight order item 224 may have fields Item ID 224a, Item Type 224b, Item Category 224c, Stop Origin 224d, Stop Destination 224e, Schedule Key 224f, and Item Sort ID 224g. The fields of the freight order item 224 can represent a combination of metadata describing the integration data object (e.g., a unique identifier, a type identifier, a category identifier, etc.), and which can be used, for example, to trigger or select rules or processes involving the integration object 220. Other fields of the freight order item 224 can represent mappings or references to particular values of the underlying data source. In some cases, the mapping or reference identifiers can be de-referenced in real-time to provide access to a current value of the data source. In other cases, the fields of the freight order item can alternatively, or additionally, stored a value associated with the mapped portion of the data source.

The freight order item Stop Origin field 224d may be used also for the header Stop Origin field 222d. Similarly, the freight order item Stop Destination field 224e may be used also for the header Stop Destination field 222e. Alternatively, the integration object 220 may have multiple freight order items, which may represent various portions of a freight order trip. In such a scenario, the header Stop Origin field 222d may come from a first freight order item, such as freight order item 224, but the header Stop Destination field 222e may come from a different freight order item (not shown).

Some fields, such as Schedule Key 224f or Item Sort ID 224g, may have values supplied by an application, such as from calculation or from user input. Such fields may be calculated or set based on other fields in the integration object 220, or from other information in an application using the integration object 220. In at least some cases, the fields 224f and 224g are not mapped to, or do not reference, values in a data source.

Objects or items of the freight order item 224 may be mapped to a data structure such as the freight order data structure 230 (with URI/SCMTMS/TOR). The freight order data structure 230 may have a data object ROOT 232 and a data object ITEM 234, as examples. In practice, such a data structure will generally be a large or complex data structure and may contain hundreds or thousands, or more, data objects. The freight order item 224 may have a selected set of fields to represent the freight order data structure 230 for a particular purpose, which may include actual data fields such as Stop Origin 224d or Stop Destination 224e that are commonly used in processing.

The root 232 of the freight order data structure may have fields Data Object Structure 232a, Document 232b, Document Type 232c, and Document Category 232d. Document field 232b of the root node 232 of the freight order data structure 230 may be mapped to Item ID 224a of the freight order item 224 in the integration object 220. Document Type field 232c of the root node 232 of the freight order data structure 230 may be mapped to Item Type 224b of the freight order item 224 in the integration object 220. Document Category field 232d of the root node 232 of the freight order data structure 230 may be mapped to Item Category 224c of the freight order item 224 in the integration object 220. In this way, the freight order item 224 in the integration object 220 is mapped directly to the freight order data structure 230.

The item data object 234 of the freight order data structure 230 may have fields Data Object Structure 234a, Item ID 234b, Item Type 234c, Item Category 234d, and subfields Schedule Key 235a, Stop Origin 235b, and Stop Destination 235c via the Data Object Structure field 234a. The freight order item 224 in the integration object 220 may have additional fields from the freight order data structure 230 mapped to it. For example, the Stop Origin field 224d in the integration object 220 may be mapped to the Stop Origin field 235b in the item 234 in the freight order data structure 230, and the Stop Destination field 224e may be mapped to the Stop Destination field 235c. In this way the freight order item 224 in the integration object both points to or references the freight order data structure 230, but also points to, references, or holds data from the freight order data structure.

Example 5—Integration Object Use by Application

Figure 3:
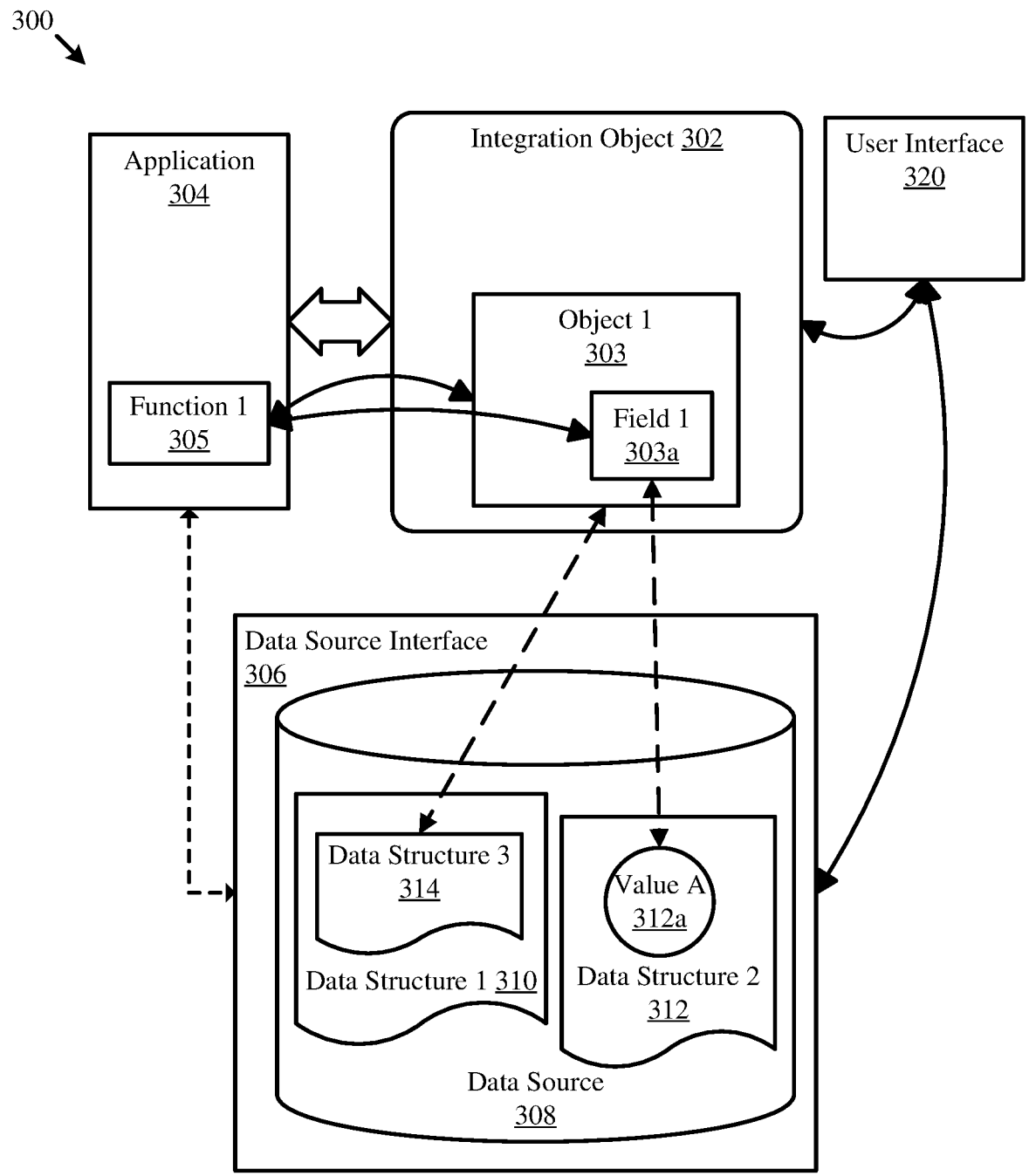
FIG. 3 is a diagram depicting use of an integration object by an application.

FIG. 3 is a diagram 300 depicting use of an integration object 302 by an application 304. The application 304 may have access to an integration object 302 and a data source 308 through a data source interface 306. The data source 308 may have internal data structures, such data structure 1 310, data structure 2 312, and data structure 3 314, which is nested within data structure 1, and values, such as a value A 312a within data structure 2. The data source interface 306 may be a specific program or interface layer for the data source 308. For example, the data source interface 306 may be specific sets of stored procedures for a database management system, or a specific set of available views for a relational database, or a specific function (or method, or procedure) for accessing a data document such as an XML file, all of which may include specific logic or rules for access, such as access permissions, read/write control, update push control, and so on.

The integration object 302 may be mapped, at least in part, to the data source 308. The integration object 302 may have object 1 303 which may be mapped to data structure 3 314. Further, object 1 303 may have field 1 303a, which may be mapped to value A 312a. The application 304 may use the integration object 302 to access the data source 308 without going through the data source interface 306. For example, application 304 may have function 1 305 that uses data structure 3 314 and value A 312a. Function 1 305 may use object 1 303 to access data structure 3 314 and field 1 303a to access value A 312a. This may simplify access, which may include speed of access, because function 1 305 avoids going through each layer of the data source 308 (the data source interface 306, the data source 308, the data structure 1 310) to get to data structure 3 314 and avoids going through a separate set of layers to get to value A 312a (the data source interface 306, the data source 308, the data structure 2 312). In another scenario, value A 312a may be in a separate data source from data structure 3 314. In this scenario, accessing the integration object 302 by function 1 305 for both value A 312a and data structure 3 314 is a single point of access compared to accessing two separate data sources, which may include several layers of access.

Further, field 1 303a may store data from value A 312a rather than merely point to or reference value A. In such a scenario, function 1 305 may obtain the value directly from the integration object 302 without de-referencing field 1 303a back to value A 312a. Additionally, in some scenarios, function 1 305 may edit field 1 303a. Such an edit may be pushed back to value A 312a in the data source 308 at a later time, such as after a confirmation to commit the change, or at a time when load on the data source 308 or the network connection is lower.

Accessing the integration object 302 may be more efficient for the application 304 than accessing the data source 308. For example, the data source 308 may be remote to the application 304, whereas the integration object 302 may be local to the application. In such scenarios, accessing the integration object 302 may be more efficient than accessing the data source 308 directly. In other cases, the application 304 may not have direct access to the data source 308, and so accessing the integration object 302 may provide additional data that otherwise may not be available to the application 304. In other scenarios, the integration object 302 may be less complex than the data source 308 (for example, the integration object may store only selected data and not the entire data set from the data source, thereby being smaller, and the stored data may be arranged in a less complex manner, such as in a less complex structure) and therefore accessing data in the integration object may require fewer resources.

In addition to being more efficient for the application 304, the integration object 302 can reduce processing load on the data source 308 by handling read, or in some cases, write, requests from the application without having to access the data source. Further, in some aspects, even when the data source 308 is accessed, such as to retrieve values to be stored in the integration object 302, the access can be more efficient. For example, values to be used in the integration object 302 can be retrieved via pinpoint queries, rather than retrieving many values in a single query, and then parsing the result to select only the needed values.

In some aspects, a user interface 320 (e.g., part of an application, which can be the same or different than the application 304, or can be provided by the data source interface 306) can provide access to the integration object 302. For example, the user interface 320 may provide functionality for creating, modifying or deleting the integration object 302. The user interface 320, when part of a separate application, can, in some cases, be used to indirectly access functionality of the application 304, as is described in Example 10. Example user interface screens for creating, modifying, or deleting integration objects are provided in Example 12.

Example 6—Simulation Using Integration Object

Use of an integration object by an application, such as shown in FIG. 3, may include simulation of various calculations or process outcomes. An application may process one or more objects in an integration object and generate one or more outcomes or values. These outcomes or values may be stored in the integration object without being saved to their corresponding data structures or data sources. The application may process these objects in several different ways, and then compare the outcomes or values of each. If a particular outcome or value is selected, that particular outcome or value may later be saved in the corresponding data structure or data source. In this way, the integration object enables simulation functionality for an application.

Further, the simulation functionality may include step-wise comparisons between different objects in the integration object. Values may be set for certain objects in an integration object, and then that object may be processed based on those values, or other objects may be processed based on the those values.

For example, under the freight unit trip plan scenario, a total cost for the trip plan may need to be calculated. Several different combinations of freight units available may be available in the integration object. The application may set various freight units as part of the trip plan and then calculate the cost based on the data in the integration object, repeating this for several different combinations until a preferred or optimal combination of freight units for the trip plan is determined. Thereafter, the preferred combination may be set in the integration object either as an object itself or as a relationship between objects, or a combination thereof. The preferred combination may then later booked or confirmed in the appropriate data sources. Alternative combinations tested may be stored as well, similar to the preferred combination, and utilized as alternative options later if the preferred combination cannot be used, thus potentially avoiding re-calculating the cost.

An integration object may have objects or sub-objects that represent alternative options to each other. For example, an integration object may have objects representing several alternate schedules for transporting a freight unit. These alternative schedules may be analyzed, such as by an application using the integration object, to determine which schedule to use. By using the alternate schedules in the integration object, the application does not need to access the underlying data sources or complex data structures represented or referenced by the integration object, or may access them directly using the integration object. This may reduce system resource usage, such as CPU utilization or bandwidth usage.

Further, when a schedule is selected, a relationship or reference between the freight unit and the schedule may be created in the integration object. For example, the object in the integration object representing the schedule may be a sub-object of the object in the integration object representing the freight unit. Further, a sequence or order of the schedules may be created, such as through an ordered (or sequential) relationship, for the freight unit, which may be represented in a field of the freight unit object or the schedule object or in the header of the integration object. Such relationships may be as shown in FIGS. 1 and 2A-B. In such a scenario, the integration object can then provide to an application the secondary schedule if the primary schedule cannot be used, such as if transport is delayed, and so on. In this way, the integration object may provide faster, real-time updates to the freight unit or a trip plan for the freight unit, without requiring accessing all related or relevant underlying data sources.

Example 7—Parallel Process Using Integration Object

Figure 4A:
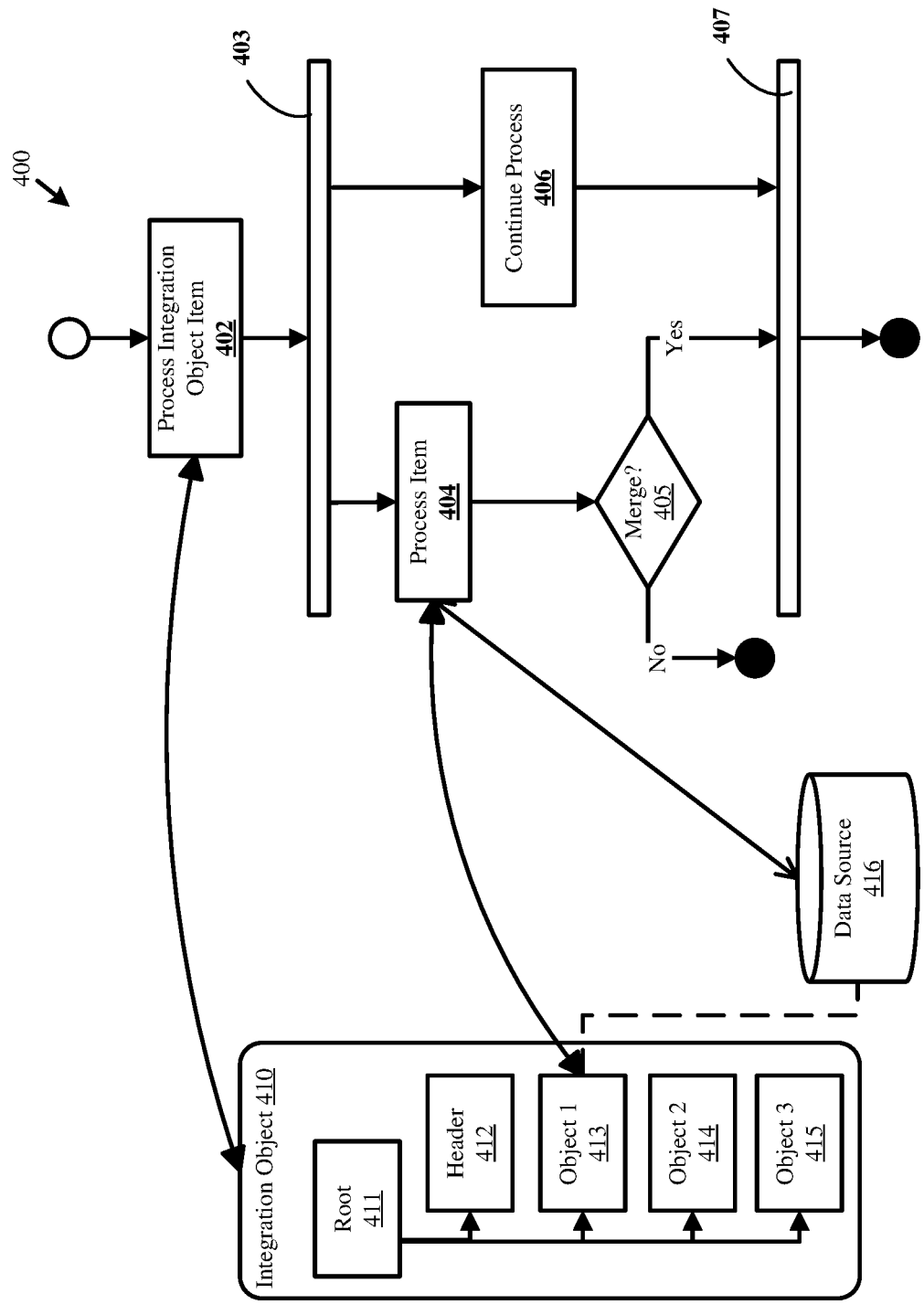
FIG. 4A depicts a process using an integration object to access a data source in parallel.

FIG. 4A depicts a process 400 using an integration object 410 to access a data source 416. A process 400 may have access to an integration object 410 which is at least partially mapped to the data source 416. The integration object 410 may have a root 411, a header 412, and objects 1-3 413, 414, 415. Object 1 413 may be mapped to the data source 416. Further, object 1 413 may also be mapped to data structures or values within the data source 416, or may have sub-objects that are additionally mapped to data structures or values within the data source 416. Additionally, object 1 413 may have values from the data source 416, which may be available for use, such as by the process 400.

The process 400 may be a software process. The start of the process 400 may be any point of a software process, which may already be running. At 402, the process 400 may begin processing the integration object 410 or a particular object or item in the integration object, such as object 1 413. Processing 102 of the integration object 410 may include performing actions, executing a function, accessing a data variable or value, or any other software action using the integration object, or part of the integration object, or data within the integration object. The process 400 may be parallelized 403 as part of processing the integration object item at 402 into two separate processes. One parallel process may process the integration object item at 404 and the other process may continue the original process at 406, performing any further steps or processes that don't immediately use the integration object item being processed at 404.

For example, processing the integration object item at 404 may include processing object 1 413 of the integration object 410. This may include accessing data in object 1 413, or using object 1 413 to access data source 416 while executing actions based on object 1 413 at 404.

After object 1 413 has been processed at 404, the process determines at 405 if it should be merged with the original process that continued at 406 or should be completed and ended. If the process at 404 for object 1 413 is complete and unneeded now, it does not need to be merged and can be completed or killed. If the process at 404 for object 1 413 is still valuable for the original process, such as having data that may be returned to the original process, it may be merged with the continued (original) process at 407. The process for using the integration object then ends; however, the actual computing process may continue and may use this process 400 again.

In one scenario, related to the freight unit trip plan example in FIG. 2B, a process 400 may be provided for booking freight orders into a freight unit trip plan. The freight unit trip plan may be represented in the integration object 410, and a particular freight unit may be represented in object 1 413. The process for booking freight orders 400 may begin processing booking particular freight orders at 402. This may include determining specific freight units, such as the freight unit in object 1 413.

When a particular freight unit is determined to need to be booked at 402, the process may create a new process to run in parallel 403 to the booking process. This new parallel process may book the particular freight unit in object 1 413 at 404 while the general booking process continues at 406. The booking process at 404 may include steps for confirming the booking with the data source 416, updating the integration object 410 to reflect the booking of the freight unit represented by object 1 413, or any other steps developed for booking a freight unit through the software.

The continuing booking process at 406 may include identifying additional freight units for booking. The process 400 may be created again in the continued process 406 when another freight unit is deemed ready for booking, such as may be represented in another object in the integration object 410.

Once the freight unit represented in object 1 413 is booked at 404, the process determines if the booking process should merge 405 with the continued booking process at 406. In this way, processing of objects or items in an integration object can be parallelized.

Example 8—Multiple Parallel Process Using Integration Object

Figure 4B:
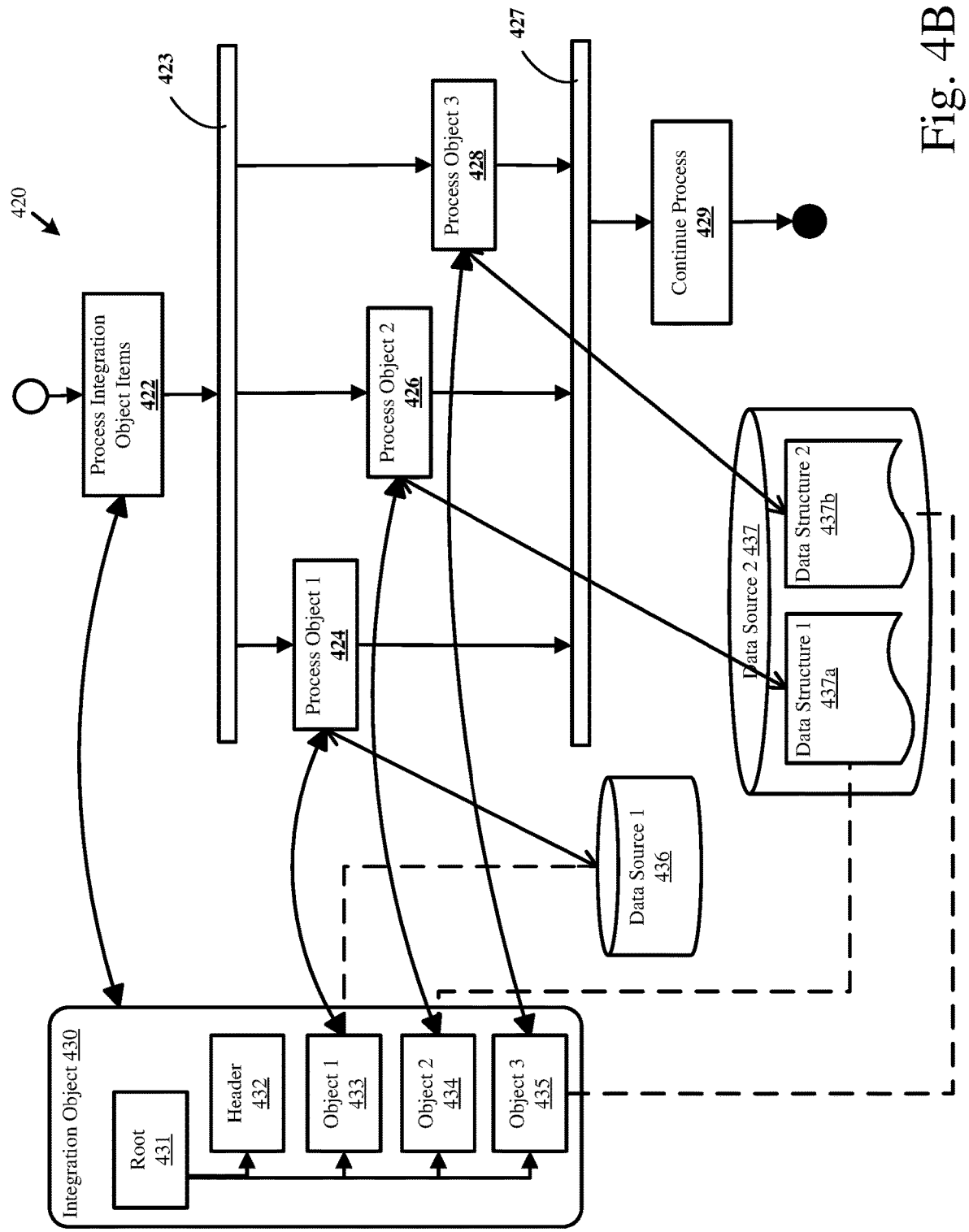
FIG. 4B depicts a process using an integration object to access multiple data sources in parallel.

FIG. 4B depicts a process 420 using an integration object 430 to access multiple data sources 436, 437 in parallel, similar to the depiction in FIG. 4A. A process 420 may have access to an integration object 430 which is at least partially mapped to the data source 1 436 and the data source 2 437. The integration object 430 may have a root 431, a header 432, and objects 1-3 433, 434, 435. Object 1 433 may be mapped to data source 1 436. Further, object 1 433 may also be mapped to data structures or values within data source 1 436, or may have sub-objects that are additionally mapped to data structures or values within data source 1 436. Additionally, object 1 433 may have values from data source 1 436, which may be available for use, such as by the process 420.

Object 2 434 may be mapped to data structure 1 437*a* in data source 2 437. Object 3 435 may be mapped to data structure 2 437*b* in data source 2 437. Further, objects 2 and 3 434,435 may also be mapped to additional data structures or values within data source 2 437 or within their respective data structures 437*a-b*, or may have sub-objects that are additionally mapped to data structures or values within data source 2 437. Additionally, objects 2 and 3 434, 435 may have values from data source 2 437, which may be available for use, such as by the process 420.

The process 420 may be a software process, and similar to the process 400 in FIG. 4A. The start of the process 420 may be any point of a software process, which may already be running. At 422, the process 420 may begin processing an integration object 430 or a particular object or item in the integration object, such as object 1 433, object 2 434, or object 3 435. Processing an integration object 422 may include performing actions, executing a function, accessing a data variable or value, or any other software action using an integration object, or part of an integration object, or data within an integration object. The process 420 may be parallelized 423 as part of processing the integration object items at 422 into separate processes for the different integration object items. Each parallel process may process a different integration object item in parallel 423.

For example, processing an integration object item at 424 may include processing object 1 433 of the integration object 430. This may include accessing data in object 1 433, or using object 1 433 to access data source 1 436 while executing actions based on object 1 433 at 424. In parallel to processing object 1 433 at 424, the process 420 may include processing object 2 434 at 426. This may include accessing data in object 2 434, or using object 2 434 to access data structure 1 437*a* in data source 2 437 while executing actions based on object 2 434 at 426. In parallel to processing object 1 433 at 424 and object 2 434 at 426, the process 420 may include processing object 3 435 at 428. This may include accessing data in object 3 435, or using object 3 435 to access data structure 2 437*b* in data source 2 437 while executing actions based on object 3 435 at 428.

Further, during the parallelization of the object processing at 424, 426, 428 between 423 and 427, the process 420 may continue the original process, performing any further steps or processes that don't immediately use the integration object items being processed at 424, 426, 428, as shown in FIG. 4A.

After objects 1-3 433, 434, 435 have been processed at 424, 426, 428 respectively, the parallelization ends and the processes merge at 427. The original process then continues at 429. Further, the continuation at 429 may re-use or invoke this process 420 again, as needed. Alternatively, each of the item processes 424, 426, 428 may separately determine if it should be merged with the other running processes or should be completed and ended separately, as shown in FIG. 4A.

In one scenario, related to the freight unit trip plan example in FIG. 2B, a process 420 may be provided for booking freight orders into a freight unit trip plan. The freight unit trip plan may be represented in the integration object 430, and particular freight units may be represented in objects 1-3 433, 434, 435. The process for booking freight orders 420 may begin processing booking particular freight orders at 422. This may include determining specific freight units, such as the freight unit in object 1 433, the freight unit in object 2 434, and the freight unit in object 3 435.

When a particular freight unit is determined to need to be booked at 422, a new process may be created to run in parallel 423 to the other booking processes. This new parallel process may book the particular freight unit in object 1 433 at 424, while another process may book the particular freight unit in object 2 434 at 426 in parallel, while another process may book the particular freight unit in object 3 435 at 428 in parallel. The booking processes at 424, 426, 428 may include steps for confirming the booking with the respective data sources 436, 437, updating the integration object 430 to reflect the booking of the freight units represented by objects 1-3 433, 434, 435, or any other steps developed for booking a freight unit through the software.

The continuing process at 429 may include identifying additional freight units for booking, or performing other actions after booking is complete, such as generating a final freight plan. The process 420 may be created again in the continued process 429 when another freight unit is deemed ready for booking, such as may be represented in another object in the integration object 430.

Further, the order of processing of objects 1-3 433, 434, 435 may be provided within the integration object, such as by a field within each object. For example, the Item Sort ID field 224g shown in FIG. 2B may be used to indicate an order to process the freight order items in the integration object. This order may be which objects to initiate a parallel process for first. In another embodiment, some or all of the objects in the integration object may not be able to be processed in parallel and may have a required order, as provided in such a field.

Example 9—Integration Reference Layer

Figure 5A:
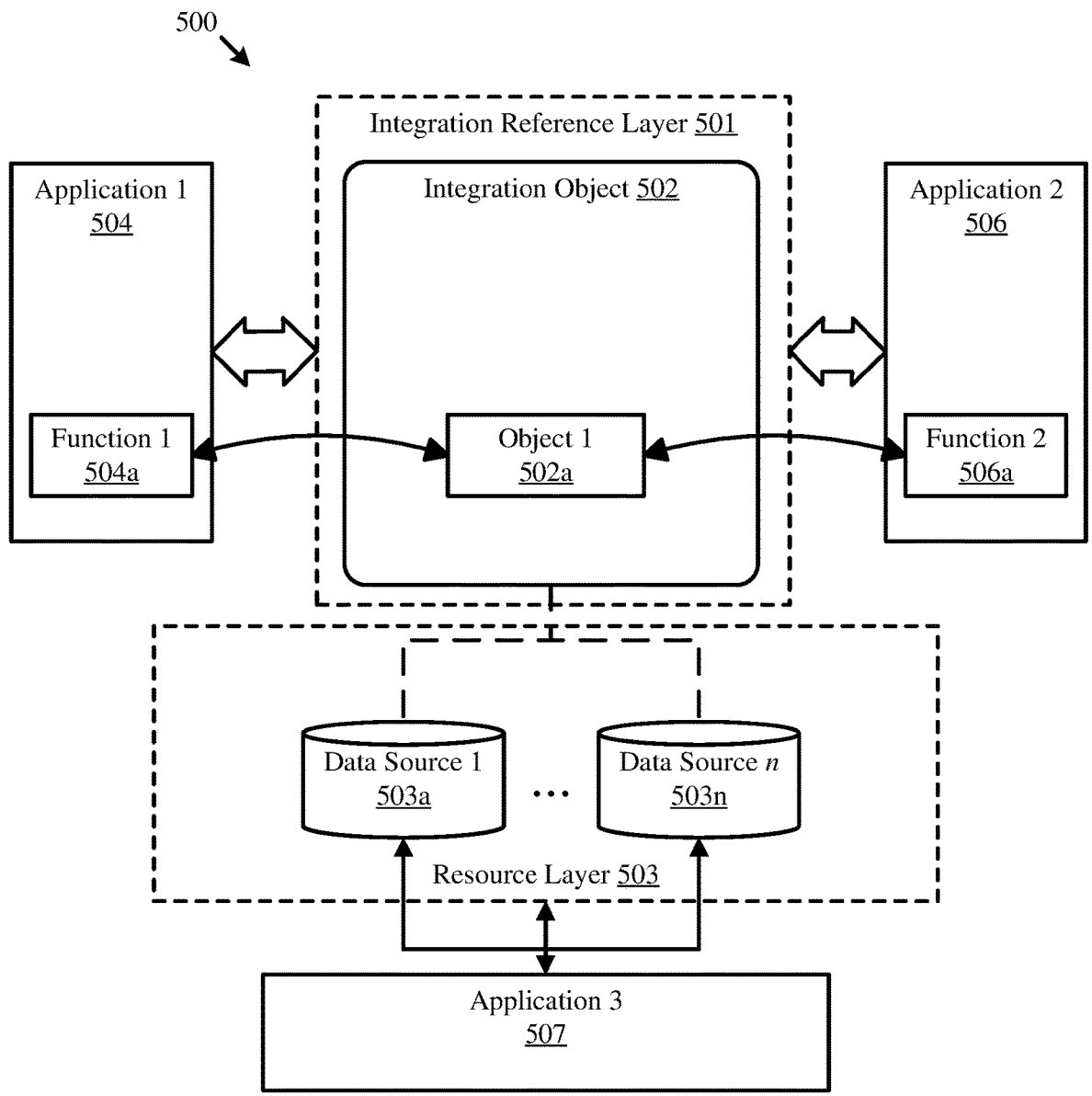
FIG. 5A is a schematic diagram of an architecture using an integration object as an integration reference layer.

FIG. 5A is a schematic diagram of an architecture 500 using an integration object 502 as an integration reference layer 501. An integration object 502 may act as an integration reference layer 501 between two software applications, such as Application 1 504 and Application 2 506. The integration object 502 may have one or more objects as described herein, such as Object 1 502a, and may be generally mapped to one or more data sources in a resource layer 503, such as data source 1 503a to data source n 503n.

The applications 504, 506 may use the integration object 502 to access the multiple data sources 503a-n as described herein; each application 504, 506 may do this independent of the other. In this way, multiple applications 504, 506 may use the same integration object 502.

Further, because each application 504, 506 may access the integration object 502, the applications may use the integration object to communicate, thus allowing the integration object to act as a reference layer 501 between the applications. For example, application 1 504 may have a function 1 504a that uses object 1 502a in the integration object 502. Function 1 504a may use object 1 502a to access the resource layer 503, or may access data from the resource layer stored in object 1. Further, function 1 504a may edit or update data in object 1 502a. Application 2 506 may have a function 2 506a that also uses object 1 502a in the integration object 502, and may use object 1 similarly to function 1 504a. Thus, function 1 504a may process object 1 502a and update some value or data in object 1 during the processing. Thereafter, function 2 506a may use the updated value or data in object 1. In this way, application 2 506 may be able to use or access functionality in application 1 504 (and vice versa); thus, the integration object 502 may act as a reference layer 501 between the applications 504, 506.

In one embodiment, the integration object 502 may represent a freight unit trip plan as shown in FIG. 2B. Application 1 504 may be tracking or management software for transportation, such as SAP Transportation Management™ of SAP SE of Walldorf, Germany Application 2 506 may be warehouse management software, such as SAP Extended Warehouse Management™ of SAP SE of Walldorf, Germany Application 1 504 may use the integration object 502 to manage freight units in real-time, while the units are being transported between terminals (such as shipping containers between ports or train stations). As the freight units are transported and arrive at their destinations early or on-time, or get delayed, Application 1 may update the freight units' respective objects in the integration object 502. Based on these changes, Application 2 504 may track available warehouse space for the freight units (or goods within the freight units). Thus, the two management programs may be integrated without requiring direct, custom interfaces, and without the overhead costs associated with the resource layer 503, as described herein.

Further, use of the integration object 502 as an integration reference layer 501 can expand the available functionality to the applications 504, 506. For example, the freight unit tracking and scheduling in application 1 504 may be able to calculate freight schedules based on part on warehouse availability as provided by application 2 506 through the integration object 502.

Additionally, the integration object 502 can act as an integration reference layer 501 for multiple applications, beyond Applications 1 and 2 504, 506.

The resource layer 503 may continue to be accessed by applications that do not access or otherwise use the integration object 502 or the integration reference layer 501. For example, application 3 507 may access the resource layer 503 or one or more of the data sources in the resource layer, such as data source 1 through n 503a-n. Application 3 507 may be a classic or previous version of an application that now uses the integration object 502, or it may be a separate program from other programs that may use the resource layer 503 and also the integration object 502, such as application 1 504 or application 2 506. In this way, an integration object 502 or an integration reference layer 501 may add functionality for some applications while not affecting the underlying resource layer 503 and other applications which may continue to use the data sources.

Example 10—Virtual Software Using an Integration Reference Layer

Figure 5B:
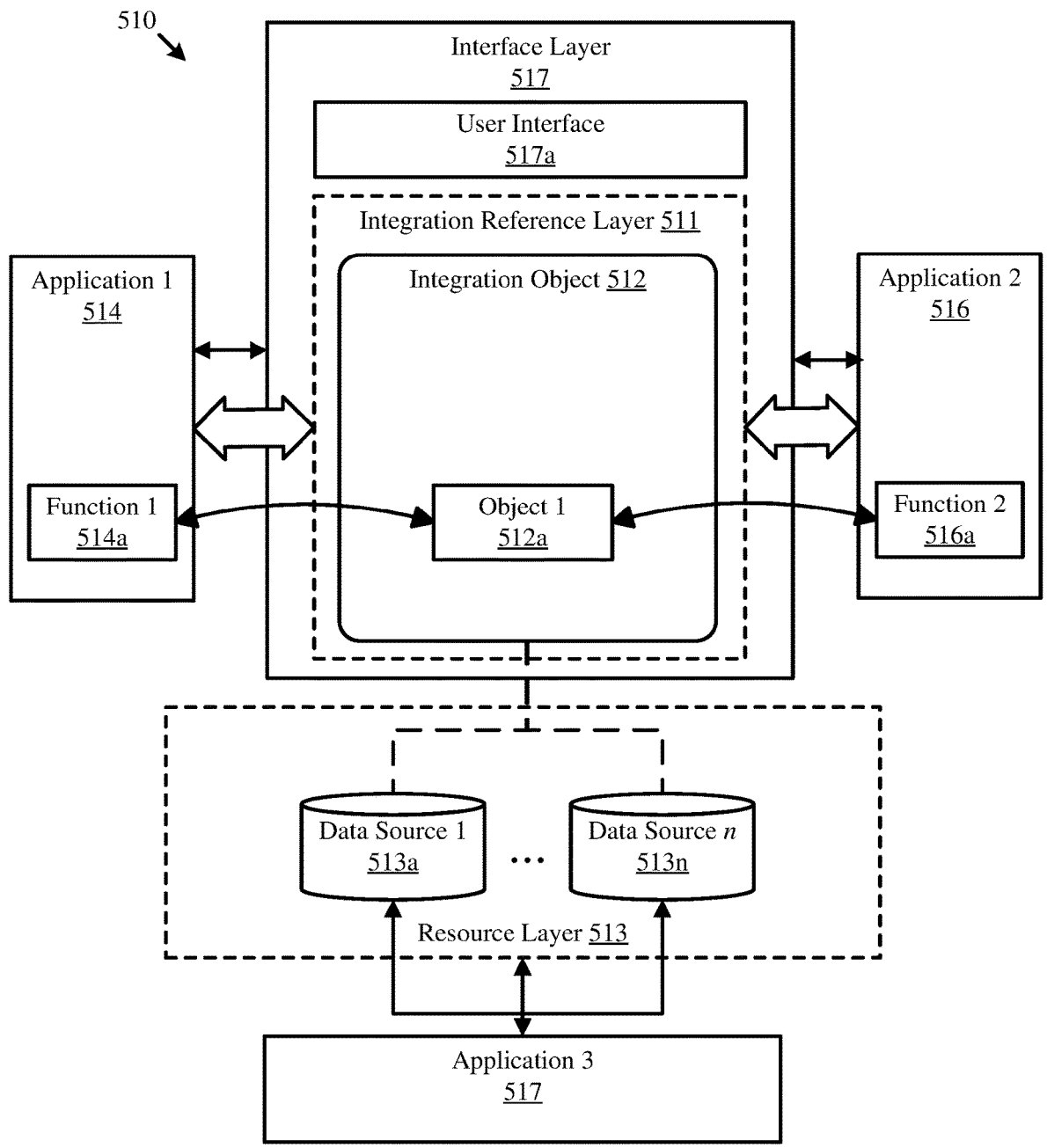
FIG. 5B is a schematic diagram of an architecture using an integration object as an integration reference layer for an interface layer.

FIG. 5B is a schematic diagram of an architecture 510 using an integration object 512 as an integration reference layer 511 for an interface layer (which can act as a virtual software application) 517. An integration object 512 may act as an integration reference layer 511 between two software applications, such as Application 1 514 and Application 2 516, as similarly shown in FIG. 5A. The integration object 512 may have one or more objects as described herein, such as Object 1 512a, and may be generally mapped to one or more data sources in a resource layer 513, such as data source 1 513a to data source n 513n.

Application 1 514 may have a function 1 514a. Application 1 514 may access the integration object 512 and, more specifically, function 1 514a may access object 1 512a. Application 2 516 may have a function 2 516a. Application 2 516 may access the integration object 512 and, more specifically, function 2 516a may access object 1 512a. The interaction shown may be similar to the interaction shown in FIG. 5A.

An interface layer 517 may be provided that uses or encompasses the integration object 512 acting as an integration reference layer 511. The interface layer 517 may be or act as a software application or a virtual software application. The interface layer 517 may have a user interface 517*a*. The interface layer 517 may be built around the integration reference layer 511 and provide functionality, through its user interface 517*a*, from one or more applications that access the integration object 512, such as Application 1 514 and Application 2 516.

The interface layer 517 may have very little functionality itself, and may be built to provide a user interface for a unique set of functionality from Application 1 514, Application 2 516, and the integration object 512. The interface layer 517 may provide functionality from Application 1 514, such as function 1 514*a*, and similarly with function 2 516*a* in Application 2 516. For example, the interface layer may call APIs provided by, or make RPCs to, the applications 514, 516. Or, the interface layer 517 may access functionality of the applications 514, 516 in another manner. In this way, a user may access the interface layer 517 through the user interface 517*a* and be able to use function 1 514*a* or function 2 516*a* without needing to access Application 1 514 or application 2 516 separately, or coordinate the processing of function 1 and function 2 separately or individually. The interface layer 517 may have functionality for coordinating, integrating, or merging functionality from application 1 514 and application 2 516.

The interface layer 517 may also be provided for a single application using an integration object, such as shown in FIG. 3. The interface layer 517 may also be provided for more than two applications using an integration object, similar to two applications as shown in FIG. 5B.

For example, application 1 514 may be tracking or management software for transportation, such as SAP Transportation Management™, and Application 2 516 may be warehouse management software, such as SAP Extended Warehouse Management™, each of SAP SE of Walldorf, Germany. The interface layer 517 may allow users to access, through its user interface 517*a*, freight unit booking options that may be executed by function 1 514*a* in the freight unit software 514 and, through the same interface layer 517, also access current warehouse usage or capacities as provided by function 2 516*a* in the warehouse software 516.

The resource layer 513 may continue to be accessed by applications that do not access or otherwise use the integration object 512 or the integration reference layer 511. For example, application 3 517 may access the resource layer 513 or one or more of the data sources in the resource layer, such as data source 1 through n 513*a-n*. Application 3 517 may be a classic or previous version of an application that now uses the integration object 512, or it may be a separate program from other programs that may use the resource layer 513 and also the integration object 512, such as application 1 514 or application 2 516. In this way, an integration object 512 or an integration reference layer 511 may add functionality for some applications while not affecting the underlying resource layer 513 and other applications which may continue to use the data sources.

Example 11—Transportation Scenario

In one scenario, an integration object as described herein may be used by transportation management software, such as SAP Transportation Management™ or SAP Extended Warehouse Management™ of SAP SE of Walldorf, Germany Other example software systems that may use an integration object include SAP NetWeaver Stack™, SAP S/4 HANA™, or SAP ERP™, each of SAP SE of Walldorf, Germany.

An integration object may be defined and instantiated, or instantiated from a predefined integration object, to represent a freight trip plan (cargo shipment) for transporting multiple cargo containers by railroad. The trip may involve multiple legs and, at some railroad stations between legs, transporting (shunting) some or all of the cargo containers to a different train. In some cases, cargo containers may need storage at a rail station while waiting for the appropriate train for the next leg of the trip. The cargo shipment may consist of hundreds of separate cargo containers.

In some cases, multiple integration objects may be instantiated to handle objects for different parts or aspects of a freight trip. For example, separate integration objects may be instantiated for each leg of a freight trip, or for each transportation vehicle in a freight trip. In some cases, an application using these integration objects may refer to multiple integration objects to make a single determination, such as when sorting objects in an integration object (e.g. to determine which objects may be used on the next leg in the next integration object and so may need to be sorted differently) or when putting objects into a relationship.

While instantiating multiple instances of integration objects may increase the load of the application runtime memory, this can generally be resolved by limiting the data stored for the objects in the integration object (such as by only storing primary key information), by considering this factor in hardware sizing evaluation, or through the use of a control framework, or a combination thereof.

Objects in the integration object may represent the cargo containers, trains, train schedules, train stations, or other real-world objects related to the freight transportation. Data representing the cargo containers, contents of cargo containers, trains, train schedules, and train stations may be stored in complex data structures in one or more data sources; such sources may store the complete set of data about the various represented items. The integration object may store only selected information for a particular purpose, which may be the information most commonly accessed for the freight trip plan about each item in its corresponding object in the integration object.

For example, an object in the integration object representing a particular scheduled train may store reference data for the train, plus only the scheduled departure date, origin location, arrival date, and arrival location, without storing other details about the scheduled train, such as train make/model, servicing information, conductor information, fuel or fuel reserves, performance data, total cars or total car load, and so on. In this way, an integration object may function as a lightweight data object by storing the minimal information necessary for processing the object. Further, the integration object may only store objects representing trains, train schedules, or train stations relevant to the freight trip plan (such as planned trains or alternative trains), rather than all trains available through a train station on the freight trip plan. In this way, the integration object may have a targeted set of objects or sub-objects, compared to the broad set of data available at the referenced data sources.

When a train represented in the integration object reaches a destination in the schedule freight trip plan, the integration object may be updated with this information, such as by the transportation software. For example, the train may arrive on schedule and the integration object may be updated to indicate this. Thus, any application using the integration object may know that the train arrived on schedule immediately, without the resource-intensive accessing of the complex data structures that represent the train, its schedule, and the scheduled trip. Further, the integration object may be accessed to determine the next steps for the cargo shipment, such as the next scheduled train for the cargo shipment (represented in the next ordered object in the integration object, or the next object related from or referenced by the just-completed leg of the trip).

Further, the next departure may be delayed, which can also be updated in the integration object and so be quickly or immediately available to the transportation management software rather than waiting on updating the complex data structures and then retrieving the data indicating the delay from the complex data structures. This may be indicated in the integration object by changing a field (or a small set of fields). This allows for faster, or real-time, analysis on how to handle the delay, such as determining to check temporary storage options or finding another departing train with availability, rather than leaving the cargo containers sitting for some time. This use of the integration object is especially useful for cargo shipments that involve hundreds of cargo containers, because it avoids the hundreds of calls to data sources for the cargo containers normally used. Further, the integration object can store alternate options, such as alternate schedules. In the case of a delay, rather than making calls to determine schedules to the various data sources for the various different potentially available trains, the transportation management software can access the integration object and change a single reference field to indicate a new relationship between the cargo containers and an alternate schedule. This available functionality significantly reduces the system resource usage and time necessary to perform the schedule change for all the cargo containers.

Figure 6A:
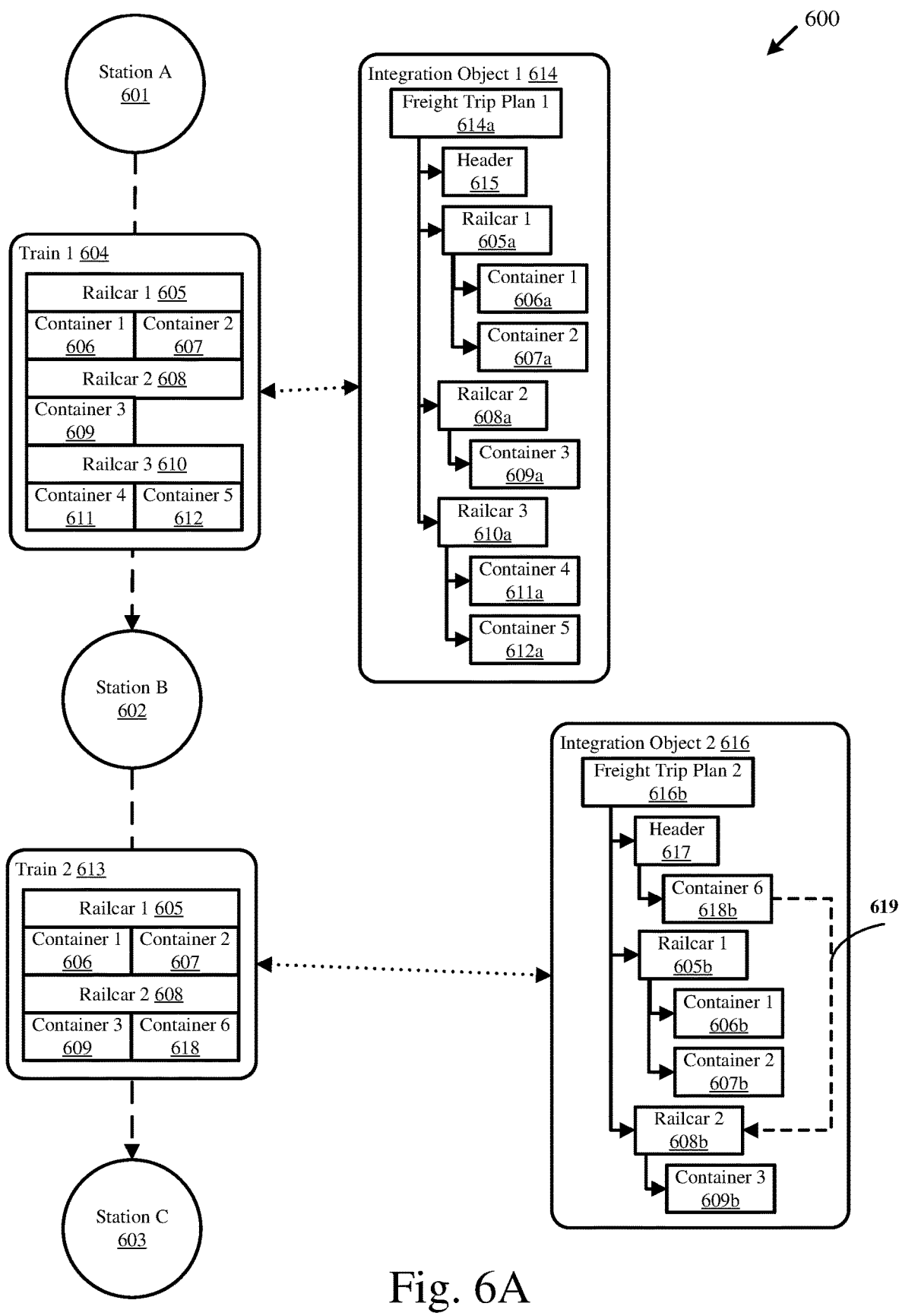
FIG. 6A depicts a transportation example using integration objects.

FIG. 6A illustrates an example use 600 of integration objects to represent transportation by train. Train 1 604 may travel from station A 601 to station B 602 carrying various shipping containers. Train 1 604 may have three railcars attached to it, railcar 1 605, railcar 2 608, and railcar 3 610. Each railcar may be able to hold up to two shipping containers. Railcar 1 605 may carry shipping container 1 606 and shipping container 2 607. Railcar 2 608 may carry shipping container 609. Railcar 3 610 may carry shipping container 4 611 and shipping container 5 612.

Train 1 604 may be represented by integration object 1 614 and may implement the freight trip plan 1 614*a* of the integration object, which may have header 615. The objects in the integration object 614 for freight trip plan 1 614*a* represent the actual train 1 604 and various railcars and shipping containers on train 1. Railcar 1 605 is represented in the integration object 614 by object railcar 1 605*a*, and railcar 1's shipping containers 1 and 2 606, 607 are represented by sub-objects, of object railcar 1, container 1 606*a* and container 2 607*a*. Railcar 2 608 is represented in the integration object 614 by object railcar 2 608*a*, and railcar 2's shipping container 3 609 is represented by sub-object, of object railcar 2, container 3 609*a*. Railcar 3 610 is represented in the integration object 614 by object railcar 3 610*a*, and railcar 3's shipping containers 4 and 5 611, 612 are represented by sub-objects, of object railcar 3, container 4 611*a* and container 5 612*a*.

After train 1 604 arrives at station B 602, train 2 613 may leave station B for station C 603 carrying a different set of railcars or shipping containers. Train 2 613 may have two railcars attached to it, railcar 1 605 and railcar 2 608. Railcar 1 605 may carry shipping container 1 606 and shipping container 2 607. Railcar 2 608 may carry shipping container 609 and now shipping container 6 618. Thus, train 2 613 may have added a shipping container and removed a railcar, but otherwise have the same actual railcars and shipping containers.

Train 2 613 may be represented by integration object 2 616 and may implement the freight trip plan 2 616*b* of the integration object, which may have header 617. The objects in the integration object 616 for freight trip plan 2 616*b* represent the actual train 2 613 and various railcars and shipping containers on train 2. Railcar 1 605 is represented in the integration object 616 by object railcar 1 605*b*, and railcar 1's shipping containers 1 and 2 606, 607 are represented by sub-objects, of object railcar 1, container 1 606*b* and container 2 607*b*. Railcar 2 608 is represented in the integration object 616 by object railcar 2 608*b*, and railcar 2's shipping container 3 609 is represented by sub-object, of object railcar 2, container 3 609*b*. The freight trip plan 2 616*b* may further have an object container 6 618*b*, which may a sub-object of the header 617 or a top-level object of the freight trip plan 2 616*b*.

The integration objects 1 and 2 614, 616 are different instantiations of integration objects for their separate freight trip plans, but may contain objects that represent the same real-world railcars and shipping containers and further point to the same underlying data structures (which represent in greater detail those real world items). Thus, for example, object railcar 1 605*a* in integration object 1 614 may point to the same underlying data structure as railcar 1 605*b* in integration object 2 616, and represent the same physical railcar, but be a separate instantiation for use in a different freight plan.

The integration objects 1 and 2 614, 616 may be used for planning, organizing, optimizing, updating, or performing other tasks for managing the freight trips between the stations. For example, integration object 1 614 may sorted based on the information from integration object 2 616 that railcar 3 610 isn't needed in the next freight trip plan, so railcar 3 may be sorted to be at the end of train 1 604 for efficient removal in station B 602. Further, object container 6 618*b* in integration object 2 616 may be put into a relationship 619 with object railcar 2 608*b* by making the object container 6 a sub-object of object railcar 2. This may be done when it is determined, in part from using integration object 1 614, that railcar 2 608 has an available ship container slot. This may be determined from integration object 1 614, by identifying that object railcar 2 608*a* has only one sub-object. Thus, planning for freight trip plan 2 616*b* can be based in part on information from freight trip plan 1 614*a*, and can thus be done before the actual train 1 604 reaches station B 602.

Example 12—User Interfaces for Integration Objects

FIG. 6B depicts a user interface screen 620 for creating, defining, maintaining or viewing an integration object. The screen 620 may have a section 622 for defining the structure of a new or selected integration object. The section 622, 624 may show or list the objects or sub-objects in the integration object, and may provide additional information, such as descriptions, about the objects or sub-objects. The screen 620 may have multiple sections for viewing or editing the integration object definition. The section 621 may have fields, such as text fields, which provide basic information about the integration object, such as the name, type, actions associated with the integration object, and other basic information. The section 622 may display the integration object, and may include the objects and sub-objects of the integration object. This may display the integration object based on how it is instantiated, with current values of the fields in the integration object. The section 623 may provide fields for the header definition of the integration object. The section 624 may provide the full definition of the integration object and include functionality to add an object or a sub-object to the integration object. The section 625 may provide fields for defining a new object or sub-object, such as a name, type, ID, or other fields. The section 625 or 623 may provide further fields and data for defining the structure of the integration object, including fields for defining locations for the integration object, a class for the integration object, a buffer for the integration object, specific database tables for the integration object or objects or sub-objects, administrative functionality such as versions or creation dates for the integration object, or other information necessary for defining or using the integration object.

Example 13—Processes Using an Integration Object

Figure 7A:
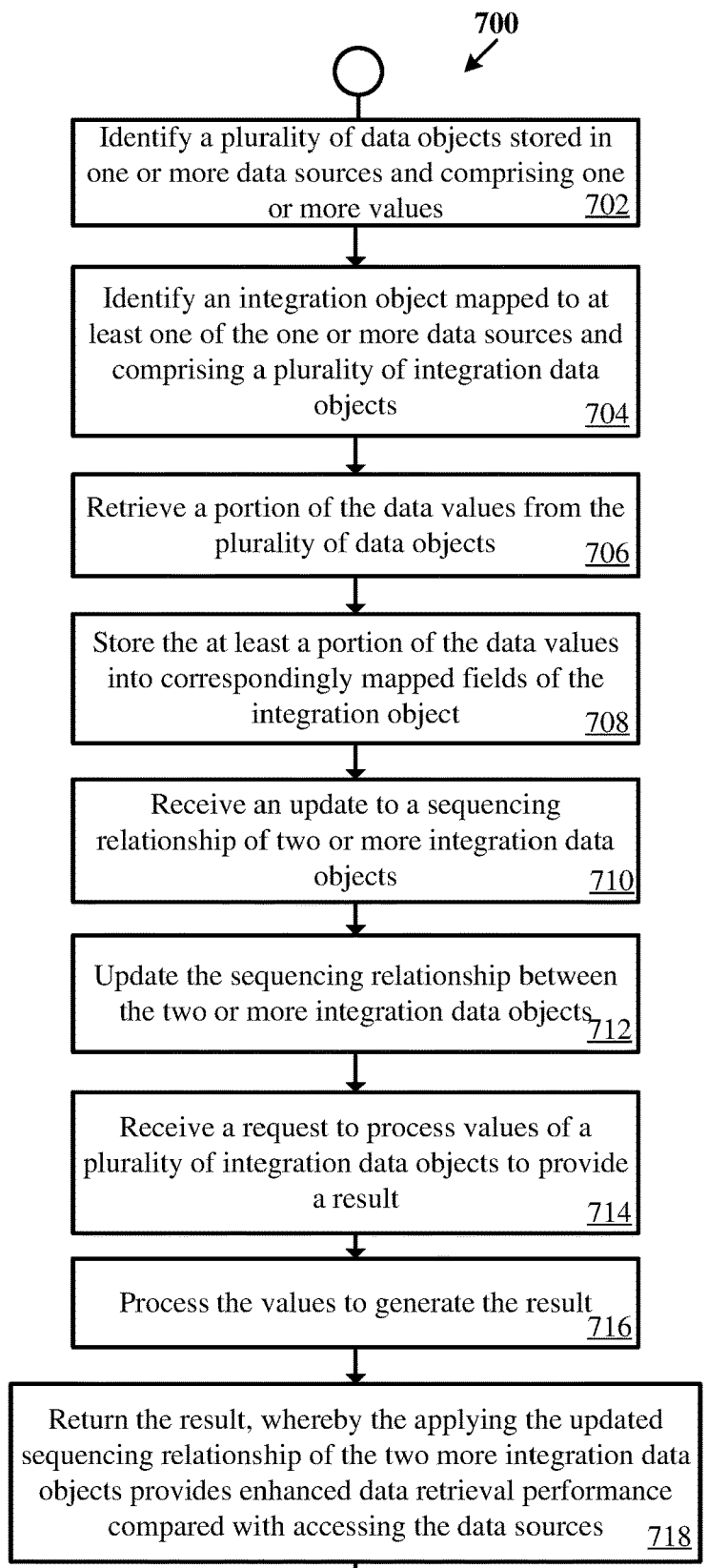
FIG. 7A is a flowchart illustrating a process for processing data requests using an integration object.

FIG. 7A is a flowchart illustrating a method 700 for processing data requests using an integration object. The method 700 can be carried out using the computing environments of FIGS. 3, 5A, and 5B, and can include features described in Examples 1-12. The method 700 can be in conjunction with, or by, an application having first access pathways to values associated with one or more data sources. The data sources can represent analog world objects, and actions or processes involving analog world objects.

The first access pathways can represent a direct or default access pathway to the data object, which can be through a first interface of the one or more data sources, which does not involve accessing the integration object. The first access pathway and interface can be, for example, issuing a query to a database system through an interface to the database system (e.g., an application that generates or issues queries to the database system). The application can have second access pathways to the values of the data sources through the integration object.

At 702, a plurality of data objects are identified. At least a portion of the plurality of data objects are stored in the one or more data sources. The plurality of data objects comprise one or more values. The integration object is identified at 704. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At 706, at least a portion of the data values are retrieved from the plurality of data objects. The at least a portion of the data values are stored, at 708, into correspondingly mapped fields of the integration object. At 710, an update is received to the sequencing relationship of two or more integration data objects of the at least a portion of the integration data objects. The sequencing relationship between the two or more integration data objects of the plurality of integration data objects is updated at 712. At 714, a request is received to process values of a plurality of integration data objects to provide a result. The values are processed to generate the result at 716. The result is returned at 718. Applying the updated sequencing relationship of the two or more integration data objects provides enhanced data retrieval performance (e.g., reduced execution time, memory use, CPU use, network use, or a combination thereof).

Figure 7B:
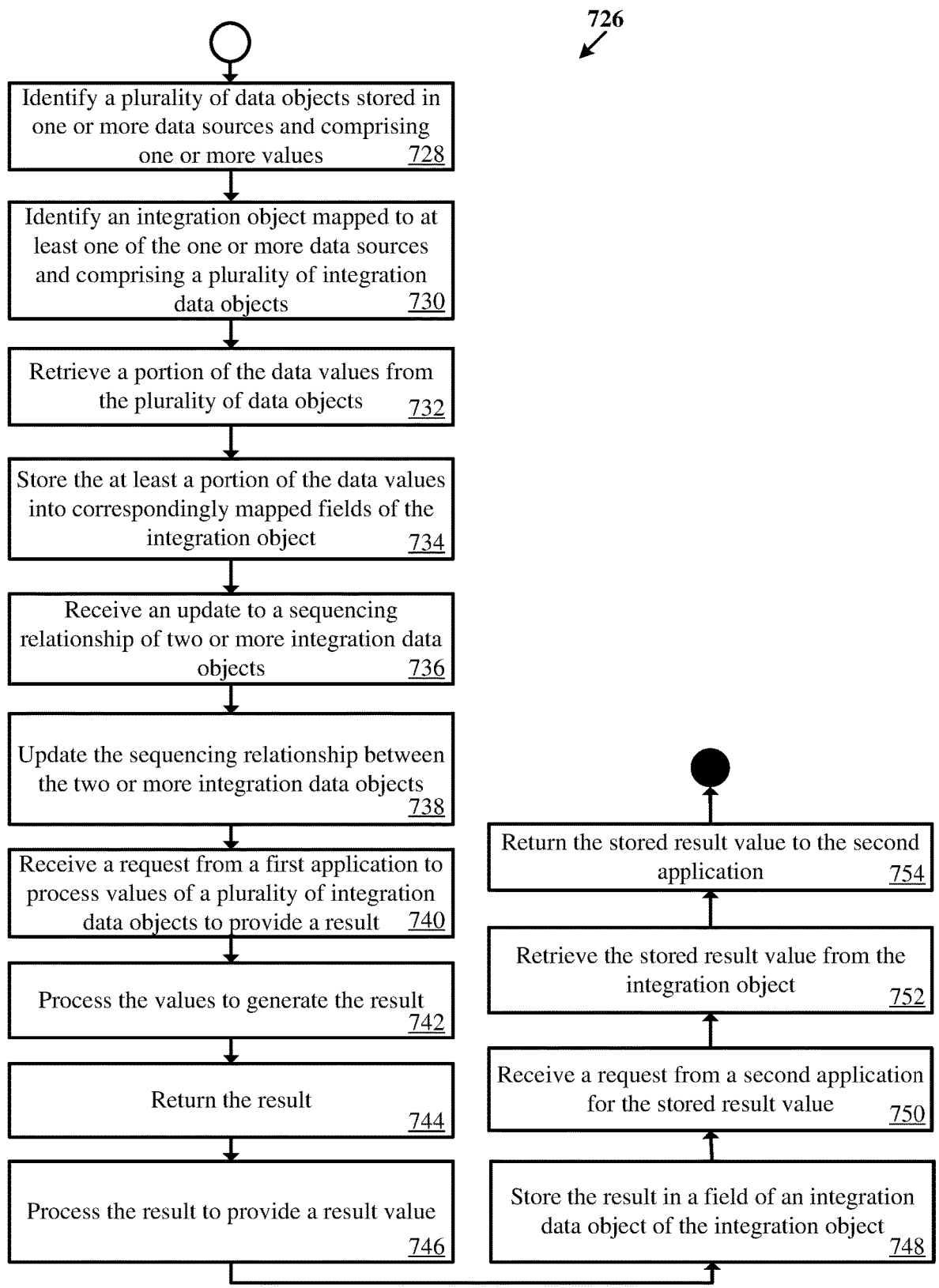
FIG. 7B is a flowchart illustrating operations for providing shared access to data in an integration object.

FIG. 7B is a flowchart illustrating a method 726 for providing shared access to data in an integration object. The method 726 can be carried out using the computing environments of FIGS. 3, 5A, and 5B, and can include features described in Examples 1-12. The data sources can represent analog world objects, and actions or processes involving analog world objects. At 728, a plurality of data objects are identified. At least a portion of the plurality of data objects are stored in the one or more data sources. The plurality of data objects comprise one or more values. The integration object is identified at 730. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At 732, at least a portion of the data values are retrieved from the plurality of data objects. The at least a portion of the data values are stored, at 734, into correspondingly mapped fields of the integration object. At 736, an update is received to the sequencing relationship of two or more integration data objects of the at least a portion of the integration data objects. The sequencing relationship between the two or more integration data objects of the plurality of integration data objects is updated at 738. At 740, a request is received from a first application to process values of a plurality of integration data objects to provide a result. The values are processed at 742 to provide the result. The result is returned at 744. Applying the updated sequencing relationship of the two or more integration data objects provides enhanced retrieval performance compared with accessing the data sources. At 746, the result is processed to provide a result value. The result value is stored in a field of an integration data object of the integration object at 748. A request is received from a second application, at 750, for the stored result value. At 752, the stored result value is retrieved from the integration data object. The stored result value is returned to the second application at 754.

Figure 7C:
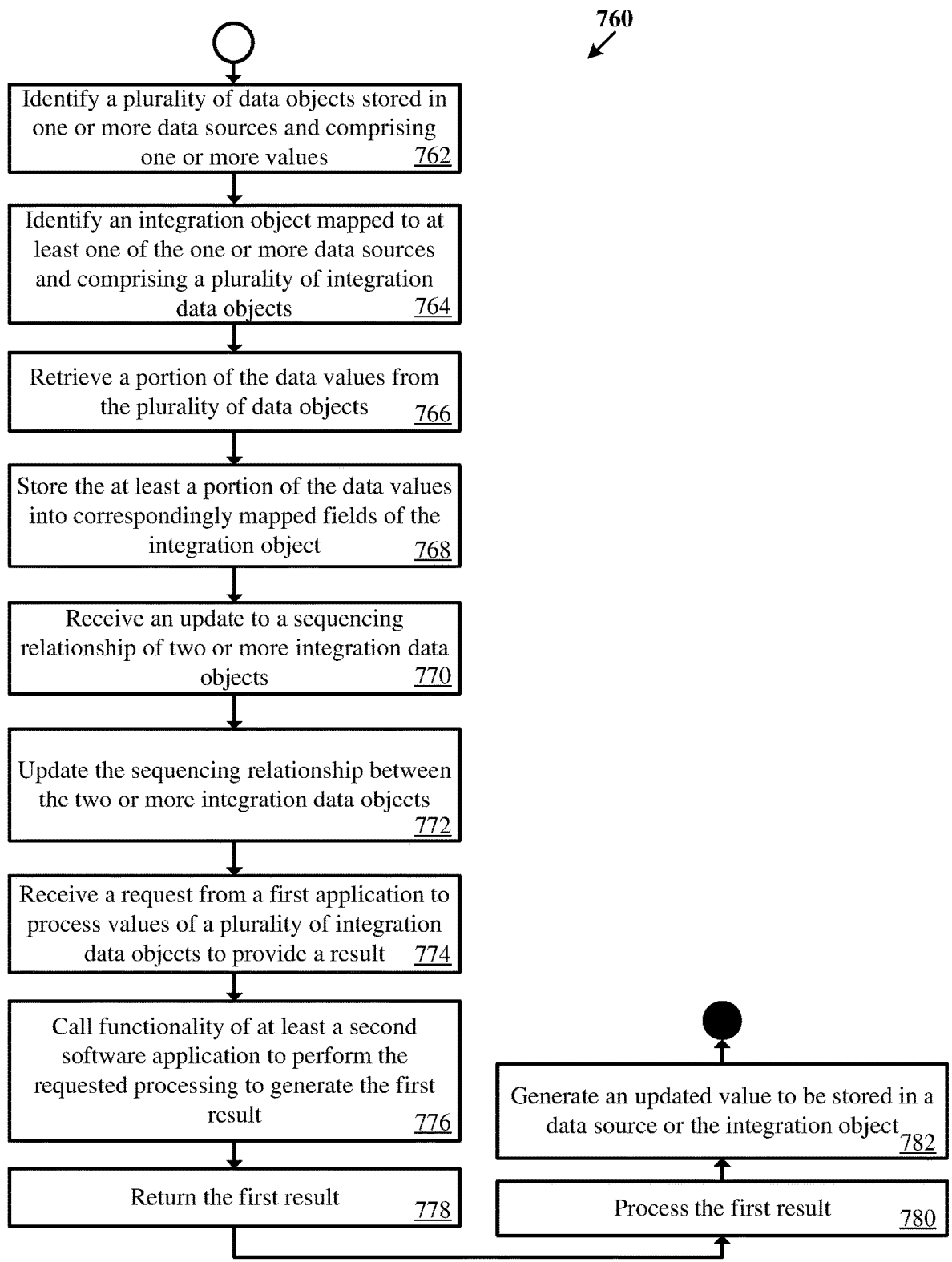
FIG. 7C is a flowchart illustrating operations for implementing an interface layer.

FIG. 7C is a flowchart illustrating a method 760 for implementing an interface layer. The method 760 can be carried out using the computing environments of FIGS. 3, 5A, and 5B, and can include features described in Examples 1-12. The data sources can represent analog world objects, and actions or processes involving analog world objects. At 762, a plurality of data objects are identified. At least a portion of the plurality of data objects are stored in the one or more data sources. The plurality of data objects comprise one or more values. The integration object is identified at 764. The integration object is mapped to at least one of the one or more data sources and includes a plurality of integration data objects. At least a portion of the integration data objects include fields representing reference information and a value. The reference information field includes an identifier of a location from which a value of a data object can be retrieved. The value field includes a value of the mapped data object. The at least a portion of the integration data objects also include a defined sequencing relationship with at least one other integration data object of the plurality of integration data objects.

At 766, at least a portion of the data values are retrieved from the plurality of data objects. The at least a portion of the data values are stored, at 768, into correspondingly mapped fields of the integration object. At 772, an update is received to the sequencing relationship of two or more integration data objects of the at least a portion of the integration data objects. The sequencing relationship between the two or more integration data objects of the plurality of integration data objects is updated at 774. At 776, a first request is received from a first application to process values of a plurality of integration data objects to provide a first result. Functionality of at least a second application is called at 778 to perform the requested processing to generate the first result. The first result is returned in response to the first request at 780. Applying the updated sequencing relationship of the two or more integration data objects provides enhanced data retrieval performance compared with accessing the data sources and the interface layer makes functionality of the second application available to the first application. At 782, the first result is processed. Based at least in part on the processing, a first updated value is generated to be stored in a data source of the one or more data sources or in the integration object.

Example 14—Computing Systems

Figure 8:
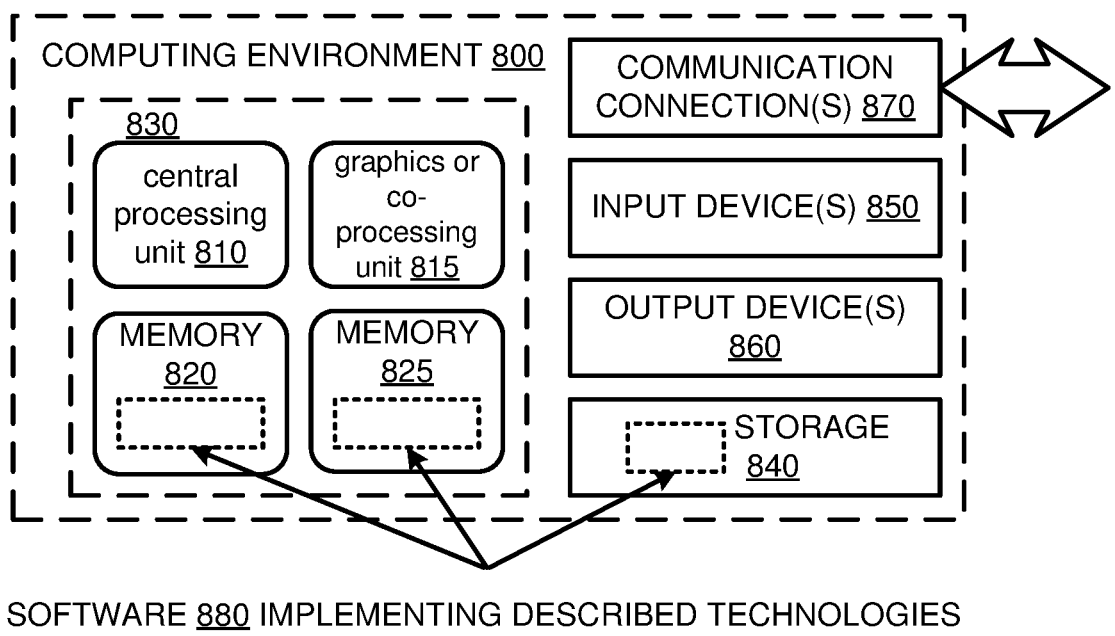
FIG. 8 is a diagram of an example computing system in which described embodiments can be implemented.

FIG. 8 depicts a generalized example of a suitable computing system 800 in which the described innovations may be implemented. The computing system 800 is not intended to suggest any limitation as to scope of use or functionality of the present disclosure, as the innovations may be implemented in diverse general-purpose or special-purpose computing systems.

With reference to FIG. 8, the computing system 800 includes one or more processing units 810, 815 and memory 820, 825. In FIG. 8, this basic configuration 830 is included within a dashed line. The processing units 810, 815 execute computer-executable instructions, such as for implementing components of the processes of FIG. 4A-B or 7A-C, or the systems of FIG. 3, 5A-B, or 6A-B, or the integration objects of FIG. 1, 2A-B, or 10. A processing unit can be a general-purpose central processing unit (CPU), processor in an application-specific integrated circuit (ASIC), or any other type of processor. In a multi-processing system, multiple processing units execute computer-executable instructions to increase processing power. For example, FIG. 8 shows a central processing unit 810 as well as a graphics processing unit or co-processing unit 815. The tangible memory 820, 825 may be volatile memory (e.g., registers, cache, RAM), non-volatile memory (e.g., ROM, EEPROM, flash memory, etc.), or some combination of the two, accessible by the processing unit(s) 810, 815. The memory 820, 825 stores software 880 implementing one or more innovations described herein, in the form of computer-executable instructions suitable for execution by the processing unit(s) 810, 815. The memory 820, 825, may also store settings or settings characteristics, such as an integration object or data associated with an integration object as shown in FIGS. 1-7.

A computing system 800 may have additional features. For example, the computing system 800 includes storage 840, one or more input devices 850, one or more output devices 860, and one or more communication connections 870. An interconnection mechanism (not shown) such as a bus, controller, or network interconnects the components of the computing system 800. Typically, operating system software (not shown) provides an operating environment for other software executing in the computing system 800, and coordinates activities of the components of the computing system 800.

The tangible storage 840 may be removable or non-removable, and includes magnetic disks, magnetic tapes or cassettes, CD-ROMs, DVDs, or any other medium which can be used to store information in a non-transitory way and which can be accessed within the computing system 800. The storage 840 stores instructions for the software 880 implementing one or more innovations described herein.

The input device(s) 850 may be a touch input device such as a keyboard, mouse, pen, or trackball, a voice input device, a scanning device, or another device that provides input to the computing system 800. The output device(s) 860 may be a display, printer, speaker, CD-writer, or another device that provides output from the computing system 800.

The communication connection(s) 870 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

The innovations can be described in the general context of computer-executable instructions, such as those included in program modules, being executed in a computing system on a target real or virtual processor. Generally, program modules or components include routines, programs, libraries, objects, classes, components, data structures, etc. that perform particular tasks or implement particular abstract data types. The functionality of the program modules may be combined or split between program modules as desired in various embodiments. Computer-executable instructions for program modules may be executed within a local or distributed computing system.

The terms "system" and "device" are used interchangeably herein. Unless the context clearly indicates otherwise, neither term implies any limitation on a type of computing system or computing device. In general, a computing system or computing device can be local or distributed, and can include any combination of special-purpose hardware and/or general-purpose hardware with software implementing the functionality described herein.

In various examples described herein, a module (e.g., component or engine) can be "coded" to perform certain operations or provide certain functionality, indicating that computer-executable instructions for the module can be executed to perform such operations, cause such operations to be performed, or to otherwise provide such functionality. Although functionality described with respect to a software component, module, or engine can be carried out as a discrete software unit (e.g., program, function, class method), it need not be implemented as a discrete unit. That is, the functionality can be incorporated into a larger or more general purpose program, such as one or more lines of code in a larger or general purpose program.

For the sake of presentation, the detailed description uses terms like "determine" and "use" to describe computer operations in a computing system. These terms are high-level abstractions for operations performed by a computer, and should not be confused with acts performed by a human being. The actual computer operations corresponding to these terms vary depending on implementation.

Example 15—Cloud Computing Environment

Figure 9:
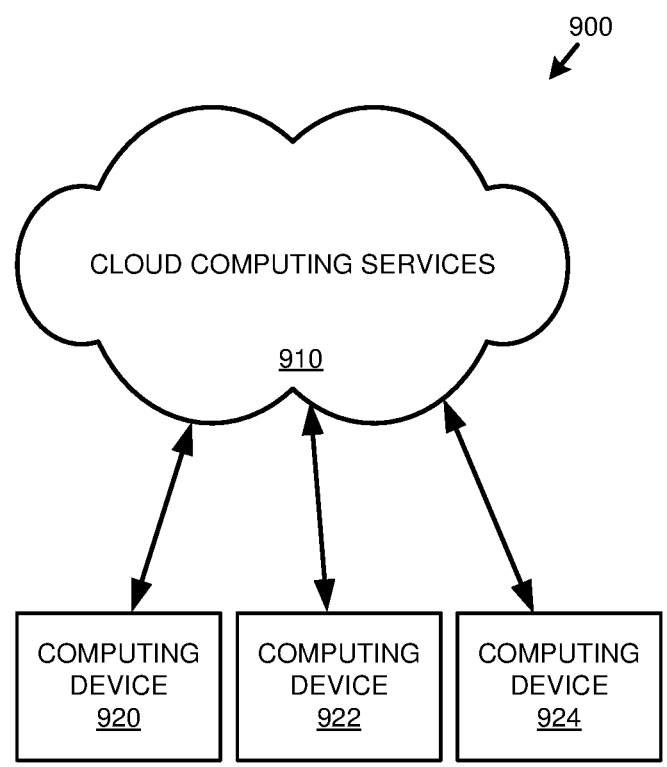
FIG. 9 is an example cloud computing environment that can be used in conjunction with the technologies described herein.

FIG. 9 depicts an example cloud computing environment 900 in which the described technologies can be implemented. The cloud computing environment 900 comprises cloud computing services 910. The cloud computing services 910 can comprise various types of cloud computing resources, such as computer servers, data storage repositories, networking resources, etc. The cloud computing services 910 can be centrally located (e.g., provided by a data center of a business or organization) or distributed (e.g., provided by various computing resources located at different locations, such as different data centers and/or located in different cities or countries).

The cloud computing services 910 are utilized by various types of computing devices (e.g., client computing devices), such as computing devices 920, 922, and 924. For example, the computing devices (e.g., 920, 922, and 924) can be computers (e.g., desktop or laptop computers), mobile devices (e.g., tablet computers or smart phones), or other types of computing devices. For example, the computing devices (e.g., 920, 922, and 924) can utilize the cloud computing services 910 to perform computing operations (e.g., data processing, data storage, and the like).

Example 16—Example Logical Data Object Schema

In any of the examples described herein, data accessed via an integration object (e.g., via a reference or mapping field of an integration data object of the integration object) can be from a logical data object. A logical data object can contain a definition of a hierarchical data structure and definitions of one or more operations that can be performed using portions of the hierarchical data structure. In some cases, a logical data object may be referred to as a "business object" and can take any number of forms including business intelligence or performance management components such as those implemented in software technologies of SAP BusinessObjects™, ORACLE Hyperion™, IBM Cognos™, and others. However, the use of logical data objects in computer applications is not limited to "business" scenarios. Logical data objects can be used to define a particular application and/or problem domain space. Aspects and artifacts of a given problem domain can be defined using the hierarchical data structure and various portions of these aspects and/or artifacts can be associated directly with definitions of relevant logical operations.

Figure 10:
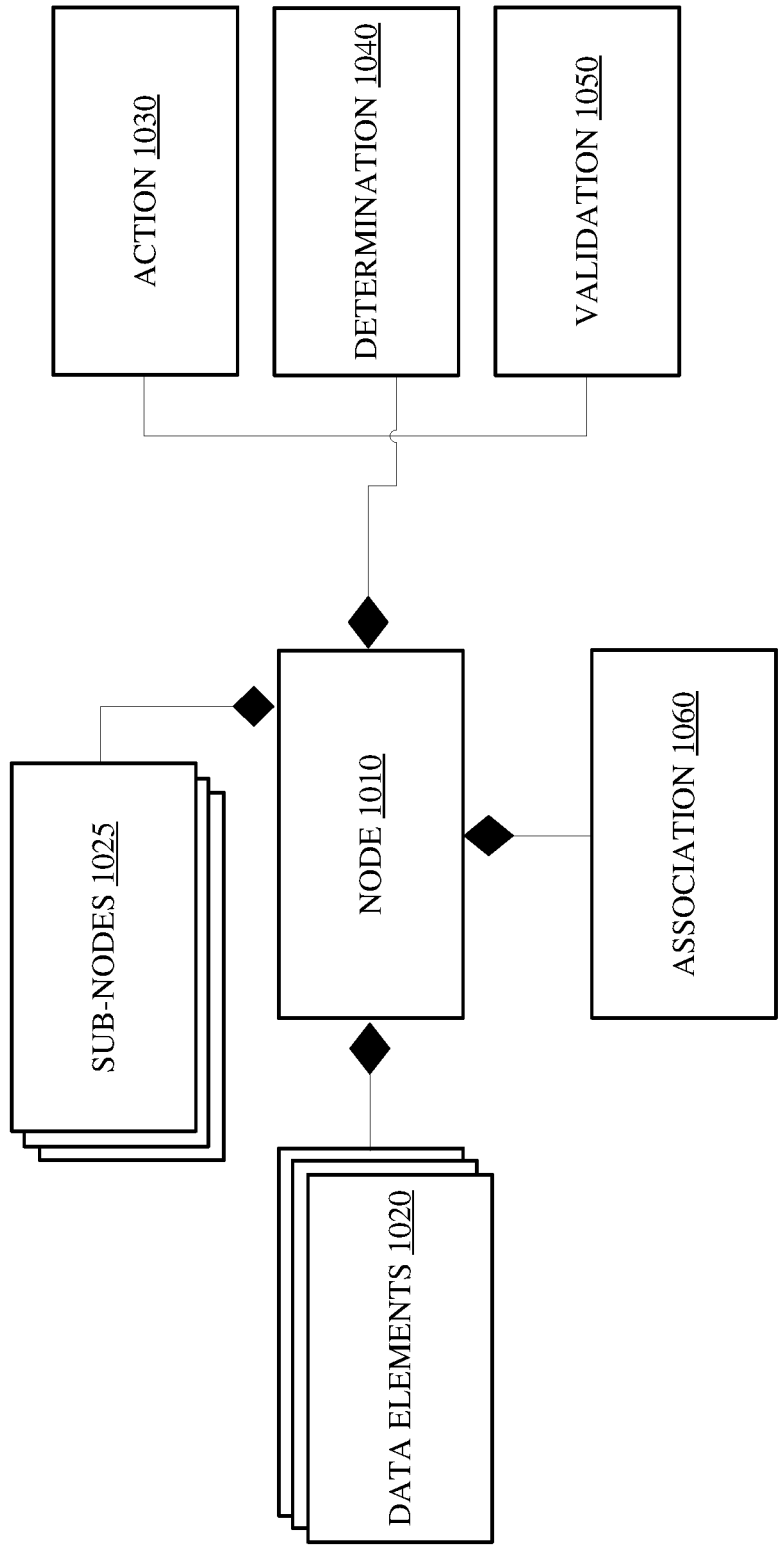
FIG. 10 is a block diagram depicting a schema for a logical data object.

FIG. 10 is a diagram of an example logical data object schema 1000. A node 1010 can contain one or more data elements 1020. A data element 1020 can contain an identifier, such as a name, and an associated value. The identifier can, for example, be associated with a field of a particular database table (e.g. via an object relational mapping, which can be to an in-memory database record or a database record stored on secondary storage). In at least some embodiments, the data element 1020 can be associated with a data type that restricts and/or validates the type of data that can be stored as a value of the data element 1020.

The node 1010 can contain one or more child nodes 1025 (also referred to as sub-nodes), which can themselves contain additional data elements 120 (and other node components, including sub-nodes 125). Combinations of sub-nodes 1010 can be used to define a hierarchical data structure of multiple nodes 1010. In at least some embodiments, the hierarchical data structure can contain a root node that does not have a parent-node and can be used as an entry point for traversing the hierarchical data structure.

Each node 1-10 in the logical data object can be associated with one or more actions 1-30. An action 1-30 can comprise a definition for a logical operation that can be performed using the node 1010 with which it is associated. The action 1030 can contain an identifier that can be used to invoke the action's logical operation. Each node 1010 in the logical data object can be associated with one or more determinations 1040. A determination 1040 can contain a definition for a logical operation that can be automatically executed when a trigger condition is fulfilled. Example trigger conditions can include a modification of the associated node 1010, a modification of the data element 120 of the associated node, the creation of a data element 1020 of the associated node, etc. A logical operation defined by an action 1030, or a determination 1040, can comprise instructions to create, update, read, and/or delete one or more data elements 1020 and/or one or more sub-nodes 125. Actions 1030 or determinations 1040 can be set to trigger, in some cases, upon the occurrence of a particular date (e.g., a particular date or a particular time on a particular date).

Each node 1010 in the logical data object schema 100 can be associated with one or more validations 1050. A validation 1050 can contain a definition of one or more data integrity rules and/or checks. The one or more data integrity rules and/or checks can be performed when the associated node 1010, and/or one or more data elements 1020 of the associated node, are created, modified, and/or deleted. Any such operation that does not satisfy the one or more data integrity rules and/or checks can be rejected.

Each node 1010 in the logical data object schema 1000 can be associated with one or more nodes from one or more other logical data objects (having the same schema or a different schema) by one or more associations 1060. An association 1060 can contain an identifier for a node in another logical data object that is associated with the node 1010. Associations 1060 can be used to define relationships among nodes in various logical data objects. The association 1060, in at least some embodiments, contains an association type indicator that identifies a type of association between the node 1010 and the node in the other logical data object.

Although the action 1030 as defined and associated with the node 1010, when the action 1030 is invoked, it targets an identified instance of the node 1010 with which it is associated. Similarly, a determination 1040 and/or validation 1050 can be defined and associated with a node 1010, but can target an instance of the associated node 1010 when it/they is/are invoked. Multiple instances of a given logical data object can be created and accessed independently of one another.

Although the instances of the logical data object share a common schema 1000, the data values stored in their respective node instances and data element instances can differ, as can the logical data object instances that are associated by the associations 1060. Additionally or alternatively, an instance of an association 1060 can identify a particular instance of an associated node in another logical data object instance. The identifier of a node instance can be an alphanumeric string that uniquely identifies the instance and, in at least some cases, can be used to look the instance up and/or retrieve data associated with the instance. Particular examples of identifiers include numerical values and universally unique identifiers. However, other types of identifiers are also possible.

Various actions may be performed using logical data objects including create, update, delete, read, and query operations. If the requested operation is a read operation, the data payload may contain a unique identifier associated with a logical data object instance to be retrieved. Processing a read operation request can comprise searching for an instance of the logical data object that is associated with the provided unique identifier in a data store, and retrieving all or part of a matching logical data object instance's data from the data store. If the requested operation is an update operation, the data payload may contain one or more values to be assigned to data element instances of an existing logical data object instance. The data payload may also contain a unique identifier associated with the logical data object instance to be updated. Processing an update operation request can comprise searching for a logical data object instance in a data store associated with the provided unique identifier and updating the matching logical data object instance with the provided data values.

Example 17—Implementations

Although the operations of some of the disclosed methods are described in a particular, sequential order for convenient presentation, it should be understood that this manner of description encompasses rearrangement, unless a particular ordering is required by specific language set forth. For example, operations described sequentially may in some cases be rearranged or performed concurrently. Moreover, for the sake of simplicity, the attached figures may not show the various ways in which the disclosed methods can be used in conjunction with other methods.

Any of the disclosed methods can be implemented as computer-executable instructions or a computer program product stored on one or more computer-readable storage media, such as tangible, non-transitory computer-readable storage media, and executed on a computing device (e.g., any available computing device, including smart phones or other mobile devices that include computing hardware). Tangible computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). By way of example, and with reference to FIG. 8, computer-readable storage media include memory 820 and 825, and storage 840. The term computer-readable storage media does not include signals and carrier waves. In addition, the term computer-readable storage media does not include communication connections (e.g., 870).

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Python, Ruby, ABAP, SQL, Adobe Flash, or any other suitable programming language, or, in some examples, markup languages such as html or XML, or combinations of suitable programming languages and markup languages. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

The disclosed methods, apparatus, and systems should not be construed as limiting in any way. Instead, the present disclosure is directed toward all novel and nonobvious features and aspects of the various disclosed embodiments, alone and in various combinations and sub combinations with one another. The disclosed methods, apparatus, and systems are not limited to any specific aspect or feature or combination thereof, nor do the disclosed embodiments require that any one or more specific advantages be present or problems be solved.

The technologies from any example can be combined with the technologies described in any one or more of the other examples. In view of the many possible embodiments to which the principles of the disclosed technology may be applied, it should be recognized that the illustrated embodiments are examples of the disclosed technology and should not be taken as a limitation on the scope of the disclosed technology. Rather, the scope of the disclosed technology includes what is covered by the scope and spirit of the following claims.

What is claimed is:

1. A method, implemented by a computing device comprising a processor and at least one memory coupled to the processor, comprising:

instantiating a plurality of data object instances, representing analog world objects, for processing, wherein the plurality of data object instances are stored in one or more data sources, the plurality of data object instances comprising one or more values;

instantiating an integration object instance, the integration object instance mapped to at least one of the one or more data sources, wherein the integration object instance comprises a plurality of integration data object instances, at least a portion of the plurality of integration data object instances being instances of an abstract data type, wherein an abstract data type defines one or more data members for the abstract data type and comprises:

data members providing fields representing:

reference information, the field representing reference information being a reference information field, the reference information comprising an identifier of a location from which a value stored in a data object instance of the plurality of data object instances can be retrieved; and a value, the field representing a value being a value field, the value comprising a value of the data object instance identified by the reference information for a data member of the one or more data members; and a sequencing data member storing a defined sequencing relationship with at least one other integration data object instance of the plurality of integration data object instances;

wherein the plurality of integration data object instances are different than, and do not include, the plurality of data object instances, and the plurality of integration data object instances used during processing of the integration object instance are not stored in the one or more data sources;

retrieving at least a portion of the values from one or more of the plurality of data object instances, the retrieving at least a portion of the values comprising, for at least one integration data object instance of the at least a portion of the plurality of integration data object instances, retrieving one or more respective values from the one or more of the plurality of data object instances, the one or more of the plurality of data objects instances being identified by one or more data members of the at the at least one integration object instance of the at least a portion of the plurality of integration data object instances providing one or more fields representing reference information;

storing the at least a portion of the values into one or more correspondingly mapped value fields of the at least one integration data object instance of the at least a portion of the plurality of integration data object instances;

receiving an update to the defined sequencing relationship of two or more integration data object instances of the plurality of integration data object instances;

updating the defined sequencing relationship between the two or more integration data object instances of the plurality of integration data object instances to provide an updated sequencing relationship;

storing the updated sequencing relationship in the sequencing data member of a least one integration data object instance of the two or more integration data object instances;

receiving a request from an application to process at least a portion of the plurality of integration data object instances to provide a result;

processing the least a portion of the plurality of integration data object instances in an order determined at least in part using the updated sequencing relationship to generate the result; and returning the result, whereby applying the updated sequencing relationship of the two or more integration data object instances provides enhanced data retrieval performance compared with accessing the one or more data sources by the application.

2. The method of claim 1, further comprising:
determining one or more attributes of the at least a portion of the plurality of data object instances;
generating the integration object instance based at least in part on the at least a portion of the plurality of data object instances, wherein the generating comprises:
generating the plurality of integration data object instances,
for the plurality of integration data object instances, assigning values to at least a portion of their respective data members based at least in part on the at least a portion of the plurality of data object instances, and
generating one or more sequencing relationships between the plurality of integration data object instances.

3. The method of claim 1, wherein retrieving at least a portion of the values from one or more of the plurality of data object instances comprises:
for each integration data object instance of the at least a portion of the plurality of integration data object instances, generating a query to retrieve a value for a corresponding mapped field of the integration data object instance from a corresponding data object instance, providing a plurality of queries, wherein the plurality of queries provides enhanced data retrieval performance compared with retrieving the values via a more general query.

4. The method of claim 1, wherein the plurality of integration data object instances are processed in an order based at least in part on the defined sequencing relationships for one or more of the at least a portion of the plurality of integration data object instances.

5. The method of claim 1, further comprising:
updating at least one defined sequencing relationship for an integration data object instance of the at least a portion of the plurality of integration data object instances based processing the result.

6. The method of claim 1, further comprising:
generating one or more output values from the processing the result; and
storing the one or more output values in the value fields of respective integration data object instances of the plurality of integration data object instances.

7. The method of claim 6, further comprising:
updating the plurality of data object instances in the one or more data sources with the one or more output values from the plurality of integration data object instances.

8. The method of claim 6, wherein at least one of the one or more output values is not stored in a mapped data object instance of the one or more data sources.

9. The method of claim 1, further comprising:
determining that at least one integration object instance is to be updated;
retrieving an updated value from a corresponding mapped data object instance of the one or more data sources; and
storing the updated value in a corresponding value field of the at least one integration object instance.

10. The method of claim 9, wherein the retrieving uses the identifier of the reference information field rather than using a first interface for obtaining information directly from a first data source of the one or more data sources.

11. The method of claim 9, wherein the retrieving uses a first interface for obtaining information directly from a first data source of the one or more data sources.

12. The method of claim 1, wherein receiving a request to update the defined sequencing relationship is based on determining that the defined sequencing relationship is invalid.

13. The method of claim 1, wherein updating the defined sequencing relationship comprises, for a first integration data object instance of the plurality of integration data object instances, updating an integration data object instance identifier for a second integration data object instance of the plurality of integration data object instances stored in the sequencing data member of the first integration data object instance with an integration data object instance identifier for a third integration data object instance.

14. The method of claim 1, wherein updating the defined sequencing relationship comprises moving a definition of a first integration data object instance relative to definitions of second and third integration data object instances.

15. One or more tangible computer-readable media comprising computer-executable instructions that, when executed, cause a computing system to perform operations comprising:

identifying a plurality of data object instances, for processing, wherein the plurality of data object instances are stored in one or more data sources, the plurality of data object instances, comprising one or more values;

identifying an integration object instance, the integration object instance mapped to at least one of the one or more data sources, wherein the integration object instance comprises a plurality of integration data object instances, at least a portion of the plurality of integration data object instances comprising:

fields representing:
a reference information field, the reference information field comprising an identifier of a location from which a value stored in a data object instance of the plurality of data object instances can be retrieved; and
a value field, the value field comprising a value of a mapped data object instance identified by the reference information field of a same integration data object instance of the at least a portion of the plurality of integration data object instances; and
a defined sequencing relationship with at least one other integration data object instance of the plurality of integration data object instances;
wherein the plurality of integration data object instances are different than, and do not include, the plurality of data object instances and the plurality of integration object data object instances used during processing of the integration object instance are not stored in the one or more data sources;

retrieving at least a portion of the values from one or more of the plurality of data object instances, the retrieving at least a portion of the values comprising, for at least one integration data object instance of the at least a portion of the plurality of integration data object instances, retrieving one or more respective values from the one or more of the plurality of data object instances, the one or more of the plurality of data objects instances being identified by one or more reference information fields of the at least one integration data object instance of the at least a portion of the plurality of integration data object instances;

storing the at least a portion of the values into one or more correspondingly mapped value fields of the at least one integration data object instance of the at least a portion of the plurality of integration data object instances;

receiving an update to the defined sequencing relationship of two or more integration data object instances of the plurality of integration data object instances;

updating the defined sequencing relationship between the two or more integration data object instances of the plurality of integration data object instances to provide an updated sequencing relationship;

storing the updated sequencing relationship in at least one integration data object instance of the two or more integration data object instances;

receiving a request from a first application to process values of a plurality of integration data object instances to provide a result;

processing the values using the updated sequencing relationship to provide the result;

returning the result, whereby applying the updated sequencing relationship of the two or more integration data object instances provides enhanced data retrieval performance compared with accessing the one or more data sources;

processing the result to provide a result value;

storing the result value in a field of an integration data object instance of the plurality of integration data object instances to provide a stored result value;

receiving a request from a second application for the stored result value;

retrieving the stored result value from the integration data object instance; and returning the stored result value to the second application.

16. The one or more tangible computer-readable media of claim 15, the operations further comprising:

calling a first interface to update a value stored in a data source of the one more data sources with the stored result value.

17. A system comprising:
one or more memories;
one or more processing units coupled to the one or more memories; and
one or more tangible computer readable storage media storing instructions that, when loaded into the one or more memories, cause the one or more processing units to perform operations comprising:

identifying a plurality of data object instances, representing analog objects, for processing, wherein the plurality of data object instances are stored in one or more data sources, the plurality of data object instances comprising one or more values;

identifying an integration object instance, the integration object instance mapped to at least one of the one or more data sources, wherein the integration object instance comprises a plurality of integration data instances, at least a portion of the plurality of integration data instances comprising:

fields representing:
a reference information field, the reference information field comprising an identifier of a location from which a value stored in a data object instance of the plurality of data object instances can be retrieved; and
a value field, the value field comprising a value of a mapped data object instance identified by the reference information field of a same integration data object instance of the at least a portion of the plurality of integration data object instances; and
a defined sequencing relationship with at least one other integration data object instance of the plurality of integration data object instances;
wherein the plurality of integration data object instances are different than, and do not include, the plurality of data object instances, and the plurality of integration data object instances used during processing of the integration object instance are not stored in the one or more data sources;

retrieving at least a portion of the values from one or more of the plurality of data object instances, the retrieving at least a portion of the values comprising, for at least one integration data object instance of the at least a portion of the plurality of integration data object instances, retrieving one or more respective values from the one or more of the plurality of data object instances, the one or more of the plurality of data objects instances being identified by one or more reference information fields of the at least one integration data object instance of the at least a portion of the plurality of integration data object instances;

storing the at least a portion of the values into correspondingly mapped value fields of the at least one integration data object instance of the at least a portion of the plurality of integration data object instances;

receiving an update to the defined sequencing relationship of two or more integration data object instances of the plurality of integration data object instances;

updating the defined sequencing relationship between the two or more integration data object instances of the plurality of integration data object instances to provide an updated sequencing relationship;

receiving a first request from a first application to process values of a plurality of integration data object instances to provide a first result;

calling functionality of at least a second application to perform the requested processing to generate the first result using the updated sequencing relationship;

returning the first result in response to the first request, whereby the using the updated sequencing relationship of the two or more integration data object instances provides enhanced data retrieval performance compared with accessing the one or more data sources and an interface layer comprising the integration object instance makes functionality of the at least a second application available to the first application;

processing the first result; and based at least in part of the processing, generating a first updated value to be stored in a data source of the one or more data sources or in an integration data object instance of the plurality of integration data object instances.

18. The system of claim 17, the operations further comprising:
calling a first interface of a data source of the one or more data sources to update a value stored in the data source of the one or more data sources with the first updated value.

19. The system of claim 17, the operations further comprising:
receiving a second request from the first application to process values of a plurality of integration data object instances to provide a second result;

calling functionality of at least a third software application to perform the requested processing to generate the second result;

returning the second result in response to the second request, whereby applying the updated sequencing relationship of the two or more integration data object instances provides enhanced data retrieval performance compared with accessing the one or more data sources and the interface layer makes functionality of the at least a second application and at least a third application available to the first application;

processing the second result; and based at least in part of the processing, generating a second updated value to be stored in a data source of the one or more data sources or in the integration object instance.

20. The system of claim 19, wherein the integration object instance is concurrently accessible to the first application, the at least a second application, and the at least a third application.

* * * * *